(12) United States Patent
Tjon

(10) Patent No.: US 12,373,943 B2
(45) Date of Patent: Jul. 29, 2025

(54) SYSTEM AND METHOD FOR DYNAMICALLY PRIORITIZING, ORGANIZING AND DISPLAYING CELLS AND TISSUE IN ORDER OF THEIR DIAGNOSTIC SIGNIFICANCE

(71) Applicant: CDx Medical IP, Inc., Suffern, NY (US)

(72) Inventor: Robert Tjon, Nyack, NY (US)

(73) Assignee: CDx Medical IP, Inc., Suffern, NY (US)

( * ) Notice: Subject to any disclaimer, the term of this patent is extended or adjusted under 35 U.S.C. 154(b) by 0 days.

(21) Appl. No.: 17/790,827

(22) PCT Filed: Feb. 8, 2022

(86) PCT No.: PCT/US2022/015588
§ 371 (c)(1),
(2) Date: Jul. 5, 2022

(87) PCT Pub. No.: WO2022/170235
PCT Pub. Date: Aug. 11, 2022

(65) Prior Publication Data
US 2024/0169519 A1 May 23, 2024

Related U.S. Application Data

(60) Provisional application No. 63/146,956, filed on Feb. 8, 2021.

(51) Int. Cl.
*G06T 7/00* (2017.01)
*G06T 11/00* (2006.01)
(Continued)

(52) U.S. Cl.
CPC ............ *G06T 7/0012* (2013.01); *G06T 11/00* (2013.01); *G06V 10/25* (2022.01); *G06V 10/764* (2022.01);
(Continued)

(58) Field of Classification Search
CPC .................. G06T 7/0012; G06T 11/00; G06T 2207/10056; G06T 2207/30024;
(Continued)

(56) References Cited

U.S. PATENT DOCUMENTS

2013/0002847 A1* 1/2013 Zahniser ................. G06T 7/136
345/682
2013/0286038 A1* 10/2013 Kamath ................ G06T 7/0012
345/592

(Continued)

FOREIGN PATENT DOCUMENTS

WO     2018076023  A1   4/2018

OTHER PUBLICATIONS

International Search Report and Written Opinion dated Jun. 29, 2022 issued in PCT International Patent Application No. PCT/US2022/015588.

(Continued)

*Primary Examiner* — Kathleen M Broughton
(74) *Attorney, Agent, or Firm* — Amster, Rothstein & Ebenstein LLP

(57) ABSTRACT

A system and method for rendering an interactive display that is used by a pathologist to review a specimen slide. The system renders a series of slides that contain all the information on a digitized slide and presents the tiles in a linear fashion in order of diagnostic significance. Additionally, tiles containing cells having a high degree of abnormality are provided with images of neighboring cells/tissue so that (Continued)

a reviewing pathologist is provided with context which is beneficial for a determination of abnormality.

9 Claims, 18 Drawing Sheets

(51) Int. Cl.
   *G06V 10/25* (2022.01)
   *G06V 10/764* (2022.01)
   *G06V 10/776* (2022.01)
(52) U.S. Cl.
   CPC .. *G06V 10/776* (2022.01); *G06T 2207/10056* (2013.01); *G06T 2207/30024* (2013.01)
(58) Field of Classification Search
   CPC .... G06V 10/25; G06V 10/764; G06V 10/776; G06V 10/82; G06V 20/698; G16H 20/10; G16H 20/40; G16H 50/20; G16H 10/40
   See application file for complete search history.

(56) References Cited

U.S. PATENT DOCUMENTS

| | | | |
|---|---|---|---|
| 2014/0193052 A1* | 7/2014 | Yoshihara | G06T 7/0012 |
| | | | 382/128 |
| 2015/0310652 A1* | 10/2015 | Dobson | G06T 11/60 |
| | | | 345/629 |
| 2019/0073511 A1 | 3/2019 | Hamilton | |
| 2019/0338038 A1 | 11/2019 | Jiang et al. | |
| 2020/0160032 A1* | 5/2020 | Allen | G16H 50/30 |
| 2020/0364587 A1* | 11/2020 | Kapur | G16H 30/40 |
| 2021/0027459 A1* | 1/2021 | Madabhushi | G06N 3/045 |
| 2021/0077009 A1* | 3/2021 | Viswanath | A61B 5/4255 |

OTHER PUBLICATIONS

EP Supplemental Partial European Search Report dated Dec. 11, 2024, issued in European Patent Application No. 22750568.2.

* cited by examiner

SYSTEM AND METHOD FOR DYNAMICALLY PRIORITIZING, ORGANIZING AND DISPLAYING CELLS AND TISSUE IN ORDER OF THEIR DIAGNOSTIC SIGNIFICANCE

CROSS-REFERENCE TO RELATED APPLICATIONS

This application is a U.S. national stage entry under 35 U.S.C. § 371 of PCT International Patent Application No. PCT/US2022/015588, filed Feb. 8, 2022, which claims benefit of U.S. Provisional Application No. 63/146,956, filed Feb. 8, 2021, the contents of which are hereby incorporated by reference.

FIELD OF THE INVENTION

The present invention generally relates to the field of identifying, categorizing and presenting potentially harmful tissues and cells. More particularly, the present invention pertains to improved computer systems and methods for analyzing digital microscope images of tissues and cells on a slide, and then dynamically identifying, prioritizing and emphasizing the specific regions on the slide that are most concerning (e.g., potentially cancerous) to enable medical professionals to make diagnoses, prognosis assessments and treatment decisions and treatment with greater efficiency and accuracy than prior techniques.

BACKGROUND OF THE INVENTION

Reviewing microscope slides containing cells is a time-consuming endeavor and it is prone to human error. For example, cytological specimens of tissue and cells are routinely obtained in different diagnostic scenarios and are manually analyzed by pathologists. In other contexts, non-lacerational brush biopsy samples of tissue are obtained using a brush that is sufficiently stiff to penetrate tissue in order to obtain an adequate sample of tissue and cells. In the process of obtaining these full thickness tissue specimens, single cells, cell clusters and tissue fragments are collected and transferred to a microscope slide which the pathologist will examine for abnormal cells (e.g., dysplasia), which as discussed below, is cumbersome, time consuming and can lead to missed diagnoses and inappropriate, non-ideal or insufficient treatments.

Other types of cell specimens that are examined by pathologists include cell block slide preparations. Cell blocks are prepared by suspending cells and tissue in a liquid medium within a tube and then centrifuging the preparation to yield a precipitate. After centrifugation, the solution is discarded, and the precipitate is embedded in paraffin or a similar medium to form a pellet. Once formed, the pellet is cut into successive slices, whereby each slice represents a cross-section of the cells/tissue on a given plane within the pellet. The slices are affixed to a microscope slide and processed for examination under a microscope by a pathologist.

No matter what biopsy technique is used to collect a tissue and cellular sample, biopsy specimens typically contain hundreds of thousands of cells randomly spread out across the surface of a slide. Cellular preparations are typically non-uniform such that there are areas on the slide that have a high cell density, other areas having a low cell density, and other areas containing no cells at all. In order to screen for and detect disease, a pathologist is required to examine all cells, cell clusters and tissue fragments on the slide. This is very challenging since it entails manually traversing through the entire surface of a slide and inspecting cells and tissue using a microscope.

The problems associated with this manual approach are manifold.

First, a pathologist will not know where to start looking on a slide for cells that are indicative of disease. Oftentimes, the pathologist will choose an area of the slide that has no signs of disease, and then must scan through the slide to seek out cells that are indicative of disease. As a result, the manual approach is more time consuming than it would otherwise be if the pathologist knew at the outset which areas of the slide are problematic and which areas have no signs of disease.

Second, a pathologist needs to move sector by sector across the slide in order to examine each area of cells. This requires the pathologist to slowly and carefully traverse a great deal of surface area on the slide to look for abnormal cells and then manually keep track of which cells have been examined, where the cells are located on the slide, and which cells are abnormal. This manual process is tedious and can often result in human error, such as the pathologist overlooking cells or tissue of interest (e.g., dysplasia, metaplasia, etc.). During screening of the slide, the pathologist first reviews a slide in low resolution to identify areas of interest. Once an area requiring further analysis is identified, the pathologist switches the microscope to a higher power to look closely at the cells and tissue. However, pathologists may miss small or isolated malignant cells in this process, in which case evidence of disease or abnormality could be missed.

Third, when a pathologist identifies an isolated cell or tissue of diagnostic interest (e.g., a malignant cell) on a slide, it would be very helpful to a pathologist to view information about the cells and tissue that are in areas neighboring the cell or tissue of interest. In this regard, as is often the case, an isolated cell or tissue of interest is not necessarily an indicator of disease. However, if the neighboring cells and tissue are also of diagnostic interest (e.g., they are also abnormal or malignant), then the likelihood of disease is much greater. Conversely, if the neighboring cells and tissue are healthy, then disease is less likely.

Computer-based systems, e.g. systems such as are provided by Indica Labs, exist that present tiles of interest associated with a determination or tag that a particular cell or tissue is of diagnostic interest. However, as the inventor of the present application has realized, such computer-based systems do not make use of computerized techniques for dynamic resizing of tiles, for example, resizing based on multiple separate identifications of diagnostic interest in neighboring areas of a slide. Rather, as the inventor of the present invention has realized, they simply present a separate tile relating to each diagnostic interest determination or tag, or simply present the entire slide.

Unfortunately, as the inventor of the present invention has realized, when examining tiles of interest generated by known computer systems, information about specifically located cells and tissue in neighboring areas simply is not available to the pathologist as the pathologist reviews a given tile or entire slide. As a result, in order to determine a presence or absence of disease, the pathologist must spend a great deal of time on the physical (or digital) specimen slide surveying the areas that neighbor a cell and tissue of concern.

The foregoing process is very time consuming and cumbersome and, it is often the case that the pathologist will discover, after spending a significant amount of time surveying neighboring areas, that such neighboring areas have no cells or tissue of interest (e.g., no abnormalities).

As the inventor of the present invention has realized, it would be a significant diagnostic benefit and efficacy improvement if the pathologist were immediately given access to information about the cells and tissue in the areas that neighbor a cell or tissue area of interest so that he or she can rule out disease or make a diagnosis with greater efficiency. Unfortunately, no such known system or method exists.

Fourth, it is very difficult for a pathologist to accurately keep track of the areas of the slide that have already been reviewed and which have not, and where abnormal cells are located. Because of these difficulties, pathologists often review the same area of a slide multiple times, which makes the process even more time consuming, wasteful of resources and can lead to even more human error.

Finally, review of such slides is generally conducted in a non-systematic and disorganized manner since cells and tissue fragments of interest (e.g., dysplastic tissue) are distributed randomly throughout different areas of the slide. As such, a pathologist could spend valuable time reviewing normal or uninteresting cells in pursuit of abnormal cells, sometimes at the expense of missing important diseased cells.

For these reasons, manual methods used by pathologists to review and analyze cells and tissue on slides is disorganized, time consuming and can often result in a missed diagnosis of disease (such as cancer).

Prior systems have been created for the purpose of performing computer-assisted analysis of specimen slides, which address some but not all of the problems associated with the manual methods used by pathologists. Such prior systems include computer and software systems created by Applicant and its predecessor (e.g., U.S. Pat. No. 6,327,377). These systems include classifiers and specially trained neural network computers that are configured to identify the most abnormal appearing cells on a specimen slide.

However, such systems only identify respective individual cells in isolation, and they do not show tissue areas neighboring the identified individual cells. In the diagnosis of abnormality associated with tissue of the gastrointestinal tract (and other body sites), it is very difficult to make a diagnosis based on a single abnormal cell. Thus, it is of critical importance for a pathologist to review the tissue that neighbors the abnormal cell to assess whether there are other abnormal cells in the same area. If a complete cluster or grouping of neighboring cells is presented to a pathologist, then the pathologist is provided with the context necessary to make a diagnosis. Thus, having information about neighboring cells would increase a pathologist's confidence and accuracy when making a diagnosis. The inventor of the present invention has realized that, unfortunately, prior techniques fail to selectively provide useful information about neighboring cells, along with the cell under consideration, based on the diagnostic interest level of the neighboring cells. Moreover, the inventors of the present invention have realized that they fail to employ computerized methodologies, such as dynamic resizing, for any such purposes.

Moreover, cells that are positive for abnormality tend to be grouped in clusters. However, prior systems typically show only one section or part, but not all, of such clusters. In particular, the inventors of the current invention have realized that current computer-based systems fail to engage in dynamic resizing of presented images associated with a cell or tissue of diagnostic significance, based on features (such as clustering) of nearby cells or tissue. Consequently, a pathologist would not consistently have the benefit of the full context of the cluster, thereby potentially hampering diagnostic accuracy. Alternatively, a pathologist may deem the partial information presented to be inconclusive and be forced to manually search for the full cluster under a microscope in order to find the information that was not displayed. This is a time-consuming process and, if the pathologist fails to find the rest of the cluster, then such failure may result in a misdiagnosis.

Although the prior systems are useful, they neither provide the pathologist with reasonable confidence that all abnormal cells have been displayed, nor that complete clusters or grouping of cell have been displayed. This is because such prior systems are not configured to make a reliable, computerized determination as to and display all abnormal cells within a dynamically resizable region of the slide, but instead only present tiles based on separate and non-aggregated consideration of subsets of such cells. Moreover, prior systems do not provide a pathologist with a means of ensuring that he or she has reviewed every single region and cell of interest on a slide. Nor do prior systems identify and organize regions of specimens that are of high diagnostic interest, and preferentially organize such regions in a smart gallery such that the pathologist will be able to focus their analysis on such regions of high interest. These shortcomings can also lead to missed or incomplete diagnoses and misdiagnoses.

As should be appreciated from the foregoing discussions, the methods used by pathologists (both with and without prior computer systems) involve a great deal of manual review of a specimen slide. However, manual review is very tedious, time consuming, error prone and can lead to missed diagnoses and misdiagnoses, and it would be advantageous to reduce the degree of manual review that is needed to make a diagnosis. When dealing with the detection of disease (such as cancer), the goal is always to minimize error and maximize accuracy. Another goal is to maximize efficiency for reviewing the slides, without sacrificing accuracy. Although prior methods have achieved a degree of success in meeting these objectives, there is a long-felt need for a system that improves upon accuracy and efficiency of the prior methods and for a system that replaces non-ordered manual review of a slide.

The problems of spatial and temporal inefficiencies in proceeding from sample slides to identification of malignancies, pre-malignancies and pathologies, as well as the issues of inefficient work duplication, misdiagnoses and accuracy are resolved by the present disclosure.

SUMMARY OF THE INVENTION

Embodiments of the invention provide a computer system for, inter alia: (1) automatically scanning and analyzing cells and tissue on a specimen slide; (2) classifying such cells and tissue by their degree of diagnostic importance; and (3) employing computerized dynamic resizing of digital slides incorporating a plurality of combined areas of interest, including in such manner where individual areas of interest have sizes determined according to computer-implemented scoring methodologies, (4) creating a gallery of image tiles corresponding to the entire specimen slide; and (5) organizing and presenting the image tiles to a pathologist in order of diagnostic importance.

Diagnostic importance is directly related to the presence of individual abnormal cells, and to a determination of whether such abnormal cells are physically or spatially grouped together. In this regard, cells that are positive for abnormality normally do not appear in isolation, but rather they are more typically grouped with other abnormal cells (e.g., in neighboring areas). Thus, a presence of a group of abnormal cells is diagnostically important, and when identified, provides a pathologist with a level of confidence that a "positive" diagnosis is accurate.

In embodiments of the invention, the system of the present invention dynamically identifies groups of diagnostically important cells (e.g., a group of abnormal cells) and then organizes such diagnostically important groups on a display (e.g. together as part of a dynamically resized tile) so that a pathologist can immediately review such groups when starting his or her analysis of a slide. In this regard, in accordance with embodiments of the invention, the system presents such diagnostically important groups to the pathologist in a manner that will enable such groups to be reviewed first. For example, in embodiments, the system generates image tiles for diagnostically important cells that will be more prominent (e.g., large image tiles) than cells that are not diagnostically significant, such as isolated cells (which will be displayed as smaller tiles).

In embodiments of the invention, the larger tiles (which are the most diagnostically significant) may be displayed first in a linear display since they contain the most important information (e.g., groups of cells and tissue of concern) needed to make a diagnosis. The isolated and/or non-grouped abnormal cells are displayed in smaller tiles and are shown after the larger tiles since they contain information of less diagnostic significance. The size of the image correlates with the number of positive events in the same vicinity. The more events in the same vicinity, the larger the image, and so the size of the image represents the higher confidence. What is the same vicinity can be determined by the cell type or cluster being examined. In general, in a sample the distance between cells is often a lot smaller than the distance between cluster of cells. In embodiments, the vicinity distance is found where the distance is larger than the distance between the cells but smaller than the distance between clusters. In embodiments, 5.5× to 6.5×, e.g., 6×, the distance between cells may be appropriate for a GI or esophageal specimen. For example, if the distance between positive events is less than 6× the distance between cells, it can be assumed those 2 events are of the same cluster. Other body sites may have a different distance. An example of vicinity is provided in FIG. 18.

In embodiment of the invention, the system analyzes a digitized specimen slide stored in digital memory and assigns a score to respective areas of the digitized specimen, for example in accordance with a degree of abnormality. That is, in exemplary embodiments, specimen areas that are deemed to be highly abnormal are provided with a high score and normal specimen areas are provided with a lower score—along a continuum of scores. In exemplary embodiments, the system uses the scores to designate areas of interest, whereby higher scores yield larger areas of interest and lower scores yield smaller areas of less (e.g., small) interest. The areas of interest are image segments or image regions that neighbor (e.g., surround) a cell or tissue of diagnostic interest. In embodiments of the invention, these areas of interest as determined by the score are used to determine how much image area surrounding a cell or tissue of interest is included in an image tile and provided to a pathologist as a unit. In embodiments, a threshold may be applied, for example, areas of interest may be designated only when the score exceeds a predetermined threshold, for example, 0.5 or 0.8.

In embodiments of the invention, once the areas of interest (e.g., groups of diagnostically important cells or geometrically-bounded shapes corresponding to regions of a digital slide) are identified using the foregoing scoring system, the system dynamically generates a series of tiles (e.g. at least initially corresponding to such geometrically-bounded shapes), each of which may contain images of cells, cell clusters, and/or tissue fragments in any combination. In embodiments, the tiles are presented on a display in a linear fashion and organized and ordered (e.g., from left to right or from top to bottom or through presentation or emphasis in a chronological sequence) according to degree of diagnostic importance (e.g., from tiles having cells of highest diagnostic importance to tiles of least diagnostic importance). Ranking can be based on neural network scores. Neural networks are trained to recognize abnormality and usually give a score between a 0 and 1, with 1 being most confident that it is abnormal. In accordance with embodiments of the invention, an entire slide is imaged and presented to a pathologist in a condensed and ordered fashion. Because, in embodiments, all of the specimen information, or all of the specimen information that has been determined through computer processing to be of diagnostic relevance, is presented, e.g. on an electronic display, in the series of tiles, the system enables the pathologist to review the tiles without the need to separately review the specimen slide. There is a finite and small probability that even though a high score has been allotted, it could be a false positive event (stochastic). To counter that, identifying neighboring positive events will ameliorate the problem. If there are multiple positive events in the same vicinity, then it is less likely that those combined events are false positives. This reflects how positive cells occur in nature, there are few of them, but if they do appear they generally appear in clusters. This allows a pathologist to review specimen slides more expeditiously and with much greater accuracy, all while reducing the likelihood of overlooking potentially harmful cells and tissues of diagnostic importance.

In accordance with embodiments, in order to create the series of tiles, a microscope slide is first digitized and then morphologically classified by a computer. As part of such automated classification, cells present on the slide are scored by a computer according to a scale for their degree of abnormality. The system uses the computer-generated score to determine how much of the image area surrounding a cell of interest is presented to the pathologist. For example, in embodiments of the invention, the higher that a cell ranks for abnormality, the greater the size of the image area neighboring the high-ranked cell is included in a tile. An r-tree data structure method may be employed. In this regard, when a pathologist detects an abnormal cell, it is important to examine the tissue and cells that neighbor the abnormal cell in order to provide an accurate diagnosis. This is because when diagnosing tissue (e.g., of the gastrointestinal tract or esophagus), one abnormal cell does not always provide enough information to make an accurate diagnosis. Rather, it is often necessary to view the surrounding tissue as well. If the neighboring cells are also abnormal or even borderline abnormal, then the pathologist will be able to make a more efficient diagnosis (e.g., quicker), and will also be able to make a more accurate diagnosis than if the neighboring cells were not included in the tile.

Thus, in embodiments of the invention, tiles of most diagnostic interest (and tiles physically grouped together, for example because the computer-implemented approaches have grouped plural contacting regions together as discussed further herein) will be larger than tiles having diagnostically non-interesting and/or isolated features since the larger tiles will include the cell of interest plus a surrounding area determined with respect to the diagnostic importance of the cell of interest and/or an accompanying neighboring positive area or areas. The larger tiles are preferentially located first, when chronologically or positionally displayed on a pathologist's electronic display, in a series of tiles because they may be the most important, and the smallest tiles are located last in the series because they are isolated and may be least important. As a result, the areas of the slide most likely to be important can be reviewed first by a pathologist, or otherwise presented to the pathologist in a manner suggesting that the pathologist should give these areas the greatest degree of the pathologist's attention.

Embodiments of the invention also eliminate "dead areas" on a slide (e.g., areas having no cells or areas having cells of less than a predetermined degree of apparent diagnostic relevance) and thus significantly reduces the two-dimensional surface area to be reviewed by a pathologist, e.g. on the electronic display, thereby reducing the time it would otherwise take to review the slide.

It is, thus, an object of the present invention to render a specimen preparation as a series or other orderly presentation of tiles so that a pathologist does not need to traverse a conventional slide, thereby reducing both the time and/or the two-dimensional slide surface area needed to be traversed by a pathologist.

It is another object of the invention to present tiles to a pathologist in preferential order according to diagnostic importance.

It is yet another objection of the invention to determine how much ancillary image context to provide to a pathologist.

It is still another object of the invention to create a linear or other ordered display from a whole slide image.

It is another object of the invention to provide a diagnostic display platform that tracks a user's review activity.

It is another object of the invention to provide a diagnostic display that allows a user to select specimen areas that are positive and/or negative for abnormality and render any of various display formats for comparing and displaying the same.

In addition, the invention addresses the problems of spatial and temporal inefficiencies in proceeding from sample slides to identification of malignancies, pre-malignancies and pathologies, as well as the issues of inefficient work duplication, misdiagnoses and accuracy, with a real-world practical solution. The processes and systems described herein effect dynamic interaction with the image data provided from an initial sample to modify the display in a fashion to effectuate spatial and temporal inefficiencies in proceeding from sample slides to identification of malignancies, pre-malignancies and pathologies, as well as the issues of inefficient work duplication, misdiagnoses and reducing the prevalence of inaccuracies. In the absence of the invention, quantification and grading of samples is slower, less quantitative and is qualitatively different.

The present invention meets the foregoing objectives with an improved computer system and method for, inter alia: (1) analyzing digital microscope images of cells and tissues that have been taken from a biopsy and placed on a slide; (2) based on a score rating the potential malignancy of cells and tissues, dynamically outputting digitized image tiles that: (a) identify and emphasize regions on the slide that contain multiple cells and/or tissue likely the most dangerous (e.g., cancerous), and thus need to be reviewed first and very carefully by a pathologist; and (b) identify and deemphasize regions on the slide where the cells are isolated (and therefore likely benign), thereby indicating to the pathologist that such regions are less important and can be quickly reviewed; (3) tracks the regions on the slide that the pathologist has reviewed, which is very difficult to do in the absence of this software; and (4) enables the pathologist to annotate the slides.

This system and method decreases the possibility of error that is associated with the above described prior methods and systems, while increasing accuracy detection and diagnosis of disease. The system of the present invention also increases the efficiency at which slides can be reviewed by a pathologist and make a diagnosis as compared to prior methods and systems, without sacrificing the accuracy of diagnostic findings.

A method of treating a cancer in a subject comprising receiving a diagnosis or identification of a cancer in a specimen from a subject wherein the cancer has been diagnosed or identified in the specimen using the method described herein administering to the subject an amount of a therapy for the diagnosed or identified cancer.

A method of reducing the likelihood of a cancer or of treating a dysplasia in a subject comprising receiving a diagnosis or identification of a dysplasia in a specimen from a subject wherein the dysplasia has been diagnosed or identified in the specimen using the method described herein and administering to the subject an amount of a therapy reducing the likelihood of a cancer or of treating a dysplasia.

In embodiments, the therapy is an anti-cancer small molecule therapy, anti-cancer radiotherapy, anti-cancer chemotherapy, anti-cancer surgery or an anti-cancer immunotherapy.

In embodiments, the therapy is a small molecule therapy, radiotherapy, chemotherapy, surgery or an immunotherapy for dysplasia.

A method of treating a cancer in a subject comprising receiving a diagnosis or identification of a cancer in a specimen from a subject wherein the cancer has been diagnosed or identified at least in part using the system or processes described herein and administering to the subject an amount of a therapy for the diagnosed or identified cancer. In an embodiment the administering healthcare provider has been provided with a full or partial diagnosis or identification of a cancer in a specimen from the subject by identification or diagnosis using the processes or methods described herein.

A method of reducing the likelihood of a cancer or of treating a dysplasia in a subject comprising receiving a diagnosis or identification of a dysplasia in a specimen from a subject wherein the dysplasia has been diagnosed or identified in the specimen using the system described herein as part of the diagnosis or identification and administering to the subject an amount of a therapy reducing the likelihood of a cancer or of treating a dysplasia.

In embodiments, the therapy is an anti-cancer small molecule therapy, anti-cancer radiotherapy, anti-cancer chemotherapy, anti-cancer surgery or an anti-cancer immunotherapy.

In embodiments, the therapy is a small molecule therapy, radiotherapy, chemotherapy, proton therapy, surgery or an immunotherapy for dysplasia. In embodiments, the surgery inserts a stent. In embodiments, the surgery removes malignant tissue. In embodiments, the cancer is an esophageal cancer or is an oral cancer. In embodiments, the esophageal cancer is an adenocarcinoma or is a squamous cell carcinoma. In embodiments, the cancer is ESCC (esophageal squamous cell carcinoma). In embodiments, the treatment comprises pembrolizumab. In embodiments, the treatment comprises nivolumab.

BRIEF DESCRIPTION OF THE DRAWINGS

The features and advantages of the present disclosure will be more fully understood with reference to the following, detailed description when taken in conjunction with the accompanying figures, wherein.

DETAILED DESCRIPTION OF THE INVENTION

Figure 1:
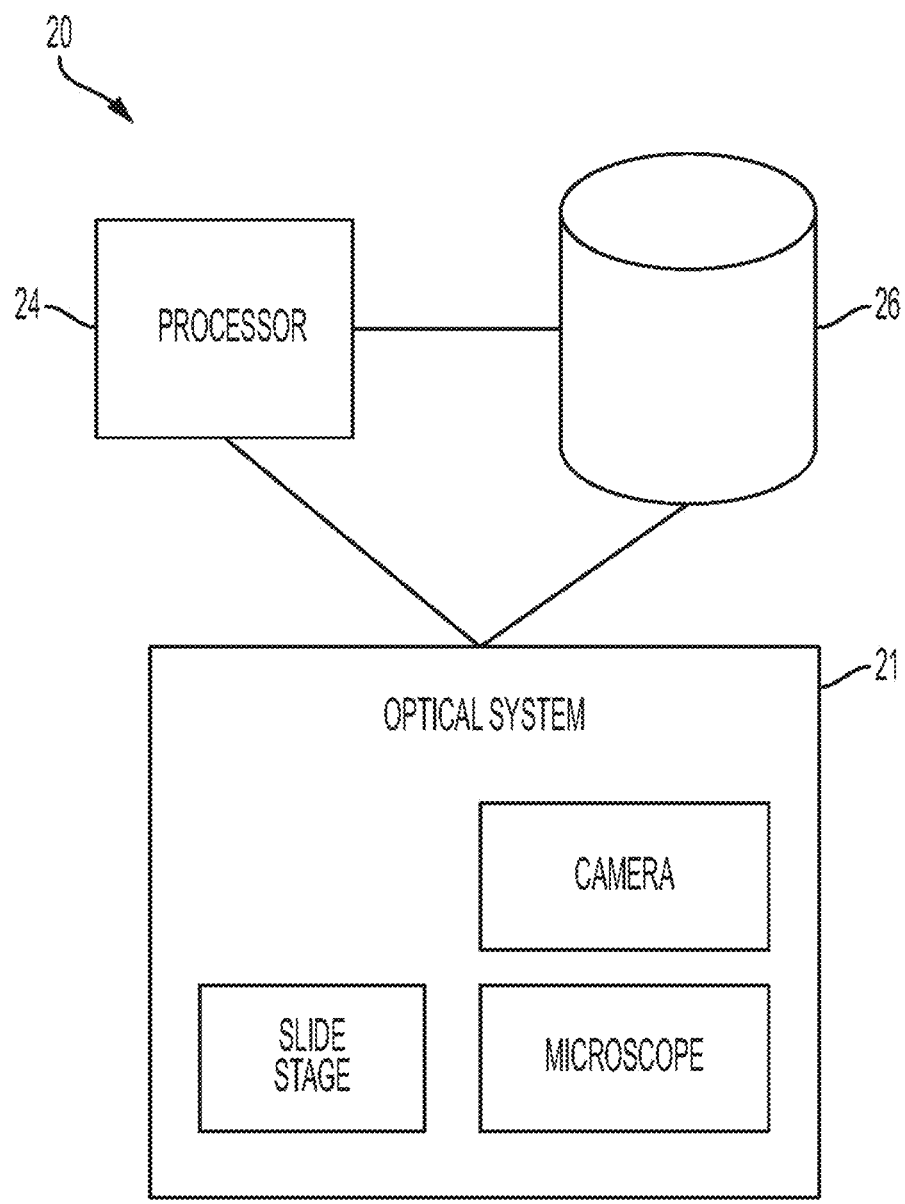
FIG. 1 is a schematic view of a system architecture in accordance with an exemplary embodiment of the invention.

Embodiments of the present invention will now be described with reference to the above-identified figures of the drawings. However, the drawings and the description herein of the invention are not intended to limit the scope of the invention. It will be understood that various modifications of the present description of the invention are possible without departing from the spirit of the invention. Also, features described herein may be omitted, additional features may be included, and/or features described herein may be combined in a manner different from the specific combinations recited herein, all without departing from the spirit of the invention.

As discussed above, the embodiments of the invention relate to digitizing cellular preparations, analyzing the digitized image for diagnostically significant information and then packaging the digitized whole slide into a series of tiles that are organized according to their diagnostic significance. The analysis includes using either algorithmic classifiers, neural network computers, or both, to detect morphological and other biological characteristics of cells and tissue. For example, such classifiers and computers may be used to identify cells having abnormal nuclear to cytoplasmic ratios tending to indicate lack of cell maturity and concomitant malignancy. In embodiments, sizes of images provided as input and/or as images of the training set of a neural net classifier may be 21×21 or 50×50 pixels, or on the order thereof, and in embodiments may be sized so as to reflect the width of two, three, or four cells in each direction. The system then identifies diagnostically significant groups of cells or tissue. Thereafter, differently sized tiles are dynamically created containing the most diagnostically significant (e.g., suspicious) groups of cells.

Typically, in the preparation of a cellular specimen for pathology, a clinician will transfer and affix cells and/or tissue to a glass microscope slide. The slide is then sent to a laboratory for further processing and medical diagnosis. Further processing may include staining the slide to enhance the contrast of the sample (or specific features of a sample)

or highlight a specific protein by using antibodies that bind to these proteins when viewed under a microscope. Such stains may include, for example, Feulgen, Papanicolaou, hematoxylin and eosin (H&E), alcian blue, and immunohistochemical stains such as for example, cdx2, muc2 and p53 to name a few. A laboratory technician may also apply a cover slip and a label to the slide.

Some cell/tissue preparations are relatively flat and occupy a two-dimensional plane. However, it will be understood that other samples may contain three-dimensionality. For example, transepithelial brush biopsy instruments which use stiff brushes to sample epithelial tissue often pick up cells, cells clusters and tissue fragments. Resultant specimens are uniquely thick, and the biologic material spread across the slide, may at least in some areas be three-dimensional in nature. Such thick, three-dimensional specimens are produced with the use of Applicant's WATS3D sampling instrument used, for example, to sample the epithelial tissue of a patient's esophagus. In embodiments, the samples are obtained by wide area transepithelial sampling. In embodiments, the samples are obtained by a brush or spatula and placed in a receptacle, such as a jar, containing a liquid fixative. In embodiments, the bristle containing portion of the brush instrument used to obtain the biological sample is clipped off from the remainder of the brush instrument and the bristle containing portion that contains the biological sample is placed in placed in a jar containing a liquid fixative. That liquid containing the sample is sent to the laboratory where the jar is opened and placed on an instrument which makes a sample slide.

Embodiments of the invention relate to scanning either conventional flat preparations, or those that are thick and three-dimensional in character.

In embodiments of the invention, for example as shown in FIG. 1, a system architecture 20 in accordance with embodiments of the invention includes an optical system 21 for obtaining a collection of images from a slide. The optical system 21 may include a microscope (e.g. a high-powered microscope), a slide positioning stage and a camera. A processor 24 for example of a computer controls the movement of the stage, e.g. in the z-direction and/or in other directions, to acquire a sufficient number of images to compose a whole-slide image of a specimen slide. The system 20 further comprises a storage device 26 for storing the acquired images. Storage device 26 may comprise a hard drive or SSD (solid state drives) or other type of memory device (e.g. a high-speed memory device), and/or distributed storage such as cloud-based storage. The processor 24 (or multiple processors working together) processes the collection of slide images in order to generate a digitized whole slide image. The processor 24 may be or may be used in conjunction with specialized image processing hardware (such as a graphical processing unit or "GPU") for increased processing speed.

It will be understood by those of ordinary skill in the art that the optical system 21 may be configured to capture and store an image after every movement of the stage, or it can alternatively be configured to capture images consecutively and continuously at regular time or distance intervals while the stage moves at a constant or variable speed, for example along the X or Y direction. In embodiments, the interval may be determined according to the average size of cell types of interest, for example, intervals of 0.25, 0.5, 0.75 or 1 cell widths. In embodiments, the interval may be determined according to the image size to be taken at each position, for example, 0.125, 0.25 or 0.5 of the image width. A serpentine or other path may be employed, so as to provide imagery of the slide as a whole. For example, movement may occur in both the X and Y directions in such a path, with results at regular and small intervals being provided to a neural network. In embodiments, a single or small number of higher scores (e.g. exceeding a threshold such as 0.5 or higher) with nearby scores along the path being low may be selectively discarded (e.g. as a likely false positive), while a longer series of higher scores may be selectively used for envelope formation, for example with the envelope being formed around a central position of the series of higher scores or of the maximally high score along the high-scoring path segment. For example, 3, 5, or 7 consecutive higher scores may be required for envelope formation, with the position of the 2nd, 3rd, 4th or median score being used for the center of the envelope. In embodiments, the number of higher scores making up the path segment may be considered in determining an initial envelope size. For example, in embodiments, the envelope size may be proportional to the number of high scores considered, or may be multiplied by a factor proportional to this number. Advantageously, this may result in the envelope size more closely matching or proportional to a size of a cell or cell cluster or tissue or other feature of potential interest. In embodiments, discovery of a position having a high score may result in changes or additions to the path, for example, with a high score (e.g. 0.9 or higher) resulting in additional pathing perpendicular to the prior path at the site of the high score for a predetermined segment length (e.g. for 3, 5, 7, 9 or 11 intervals or captures). Focusing, e.g. in the z direction, may be performed manually or automatically. In embodiments of the invention, the consecutive and continuous approach may be faster at generating a digitized whole slide image. In embodiments, commercial scanners may be employed, such as those of APERIO or 3DHISTECH.

In embodiments of the invention, specimen slides that are three-dimensional in nature undergo additional processing prior to being examined by either a pathologist and/or a computer system. Specifically, captured digital microscope images of the cellular specimen may be further processed by an enhanced EDF system which produces an enhanced, in-focus digital image that preserves diagnostically important objects and their spatial relationships to one another. This increases the accuracy of the computer analysis system as artifacts and false images are reduced and the diagnostically important objects of interest are presented to the computer in focus. For example, in embodiments of the invention, specimen slides are digitized in accordance with the image processing techniques set forth in U.S. Pat. No. 8,199,997, the contents of which are fully incorporated by reference herein.

In embodiments, cell or tissue imagery, for example esophageal cells or tissue imagery, may be obtained using a brush-based sampling technique (e.g. using a WATS or WATS-3D brush, or wide area transepithelial sampling technique and instrument). In embodiments, such an approach may be used for supplying an input for analysis by the systems as discussed herein, for providing imagery to a library that may be used in a training set of a neural network as discussed herein, or for both.

After a specimen slide is digitized, the digital image of the slide is analyzed by a processor (e.g., 24), e.g. of a computer, to detect cells, cell clusters and tissue fragments of interest. In embodiments of the invention, a digitized whole slide image is initially processed by an algorithmic classifier and then, secondarily, by a neural network computer. The algorithmic classifier locates a first group of candidate objects within the digitized image which could be the nuclei of cells.

The digitized image may then secondarily analyzed by a neural network computer. In embodiments, an algorithmic classifier or neural network may also calculate a score for cells. For example, the numeric amount of the score may correlate to the presence or seeming or probabilistic presence of morphological features, such as those associated with, e.g., cancerous or dysplastic cells. Algorithmic classification is generally described in U.S. Pat. Nos. 5,939,278, 5,287,272 and 6,327,377, all of which are incorporated by reference herein. Suitable neural networks include a convolutional neural network.

In embodiments of the invention, the improved algorithmic classifier identifies individual cells having features of diagnostic interest, for example, morphological attributes consistent with dysplastic or cancerous cells. In embodiments of the invention, such classification may be performed by a neural network, e.g. implemented on the processor 24 in combination with the storage 26, trained to recognize cells or cell clusters most likely to represent dysplastic or cancerous cells or cell clusters. In embodiments of the invention, the neural network may be used to provide a secondary classification, after the algorithmic classifier. In embodiments of the invention, the neural network is provided, as an input, an image or images identified by algorithmic classifier in the first pass. The neural network may be trained with a training set comprising a plurality of images of cells or tissue tagged with scores according to their morphological characteristics. In exemplary embodiments, the images may be obtained from, or stored in, a database having at least one set of library images. In exemplary embodiments, the images may be tagged with an indication, for example one previously assigned by a pathologist, of whether the cell or tissue has the abnormal condition (for example with 1 associated with a positive diagnosis or assessment and 0 associated with a negative diagnoses or assessment). In other embodiments, library images of a lower degree of diagnostic certainty may be assigned a probabilistic score, for example 0.5. In other embodiments, the scores may be assigned according to a different scale, for example 0 to 100 (e.g., indicative of a probability indicated as a percentage), to name one.

In embodiments, the training set data may include filtered image data, for example filtered according to whether several pathologists have each agreed, or agreed at more than a set percentage (for example, 80%) with the evaluation. Such assessments may be provided, by one or several pathologists, for example, through the display and evaluation methodologies discussed elsewhere in this disclosure. In embodiments, these results may be electronically transmitted, for example, over a secure connection via the Internet, to a processor associated with the neural network or neural networks so as to enable training data to be filtered accordingly.

In embodiments of the invention, the cell or tissue under examination may be selectively supplied to a plurality of neural networks trained with image data. For example, in embodiments of the invention, the cell may be provided as an input to a neural network trained (e.g. according to a library) with clear or relatively clear images of normal and abnormal cells labeled as such (e.g. 0 or 1). In the event that the result determined by such neural network is insufficiently definite (e.g. a result between 0.3 and 0.7), the input may be selectively provided to a second neural network trained with a training set including images (e.g. from a second library or pertaining to images for which the evaluation has varied between pathologists) of less clear or edge cases for cells or tissues, tagged by pathologists with whether they nonetheless represent a normal or abnormal condition. Thereby, assessment may be made through an image set more applicable to the input cell or tissue image. In exemplary embodiments, further passes may be performed, for example according to further libraries of images or portions thereof used as a training set for a neural network involved in the scoring, in an iterative fashion. In embodiments, different neural networks or different training sets may be used trained according to images pertaining to specific cell types, particular abnormal conditions, or both.

In embodiments, optimization of the neural network may be performed, for example, as a result of evaluating whether scoring output by the neural network is consistent with a later evaluation by a pathologist, or by a vote or average evaluation of several pathologists, pertaining to an associated tile (e.g., while being reviewed using such display functionality as is discussed elsewhere in the application). For example, weights associated with the neural network, which may e.g. determine the degree of importance in the output score that a particular image in the training set may have, may be adjusted. In embodiments, this may occur according to a backpropagation process, and may be based on a gradient function pertaining to an error curve associated with the neural network or the training data. In embodiments, such optimization may be performed on a convolutional neural network.

In embodiments, a neural network and/or training set may be specifically selected according to an initial classification, for example that of the improved algorithmic classifier. For example, if the algorithmic classifier identifies cells that appear to be dysplastic, a neural network trained with cells of varying degrees of apparent diagnosability of being dysplastic may be selectively employed, while if the algorithmic classifier identifies cells that appear to be cancerous, a neural network trained with cells of varying degrees of apparent cancer may be selectively employed.

In accordance with embodiments of the invention, the neural network computer is trained to assign scores to respective images within the digitized image according to a likelihood that a given image is likely to represent morphologic abnormality associated with dysplasia or cancer. Cells and objects that are likely to be abnormal are given a high score by the neural network computer, whereas, objects having a low likelihood of being abnormal are given a low score. For example, in embodiments, scores may be assigned on a 0 to 1 scale based an apparent likelihood of having the abnormal characteristic. For example, in embodiments, a cell exhibiting morphological characteristics of a benign cell may receive a neural net score of or around 0.1 while a cell closely approximating a known malignant image may be given a score of or around 0.9. Cells that appear somewhere between these limits will be given a score somewhere in between the range, for example of or around 0.5 or between 0.3 and 0.7. Thus, in exemplary embodiments, the range of output of the trained neural network presents a continuum corresponding to the degree of certainty that a cell abnormal. In exemplary embodiments, the processor 24 and/or storage 26 may track the classification, for example for presentation to the pathologist via a display, or for use in the computerized dynamic resizing and presentation processes discussed herein.

Figure 2:
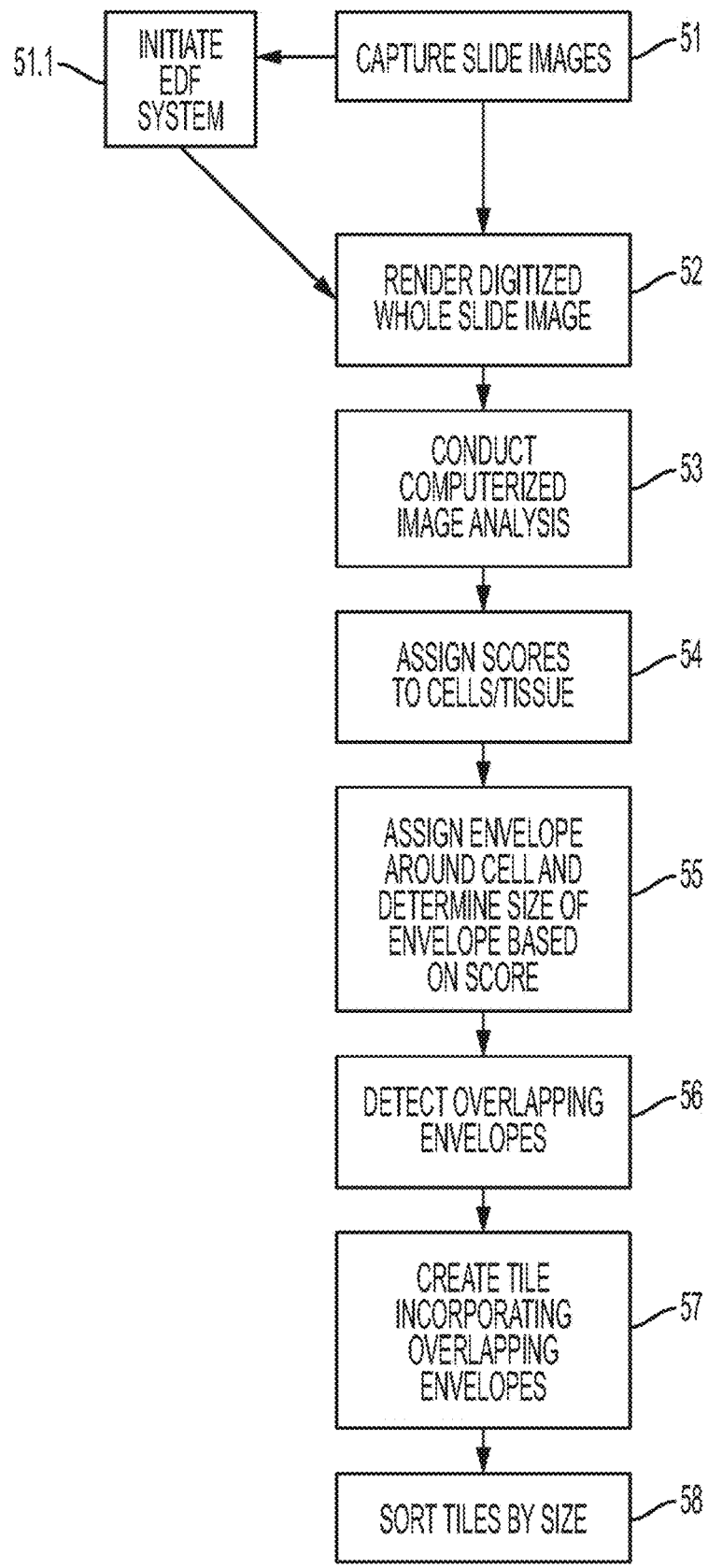
FIG. 2 is a flow chart showing exemplary steps for dynamically creating tiles in accordance with an exemplary embodiment of the invention.

In embodiments of the invention, the system uses the output score of the neural network (alone or in combination with additional information, e.g. the classification) to determine the amount of information to accompany a given cell of interest. For example, with reference to the flow chart shown in FIG. 2, initially, a microscope slide is passed through the optical system which systematically captures images of the slide in step 51. In the event that the slide to be digitized is three-dimensional in character, an Extended Depth of Focusing (EDF) routine may be initiated (step 51.1) to capture the diagnostic information and preserve spatial relationships between cells. In step 52, a digital image of the microscope slide is rendered, e.g. by processor 24, and stored on a computer or a digital storage medium such as storage 26. Next, in step 53, the computer conducts image analysis to detect diagnostic objects of interest. In step 54, a neural network computer assigns scores to respective cell images based on the cells' degree of abnormality. In step 55, the system assigns an image area extending outward from respective cells of interest, referred to as an "envelope" herein.

In exemplary embodiments, the neural network scores may be based, in addition to or instead of the features discussed above relating to the probability of an abnormal condition, on the size, shape and/or optical density of a cell nucleus, or such other cell features as may be determined to be of diagnostic relevance. In this regard, and for example, according to embodiments, a cell exhibiting a highly atypical nucleus may be afforded a larger score (and accordingly a larger sphere of influence based on its larger envelope). Thus, for example, in exemplary embodiments, a cell having a large nucleus (which may indicate an aneuploid condition indicative of dysplasia or cancer) may receive the benefit of additional context for a pathologist to make a diagnosis.

Figure 3:
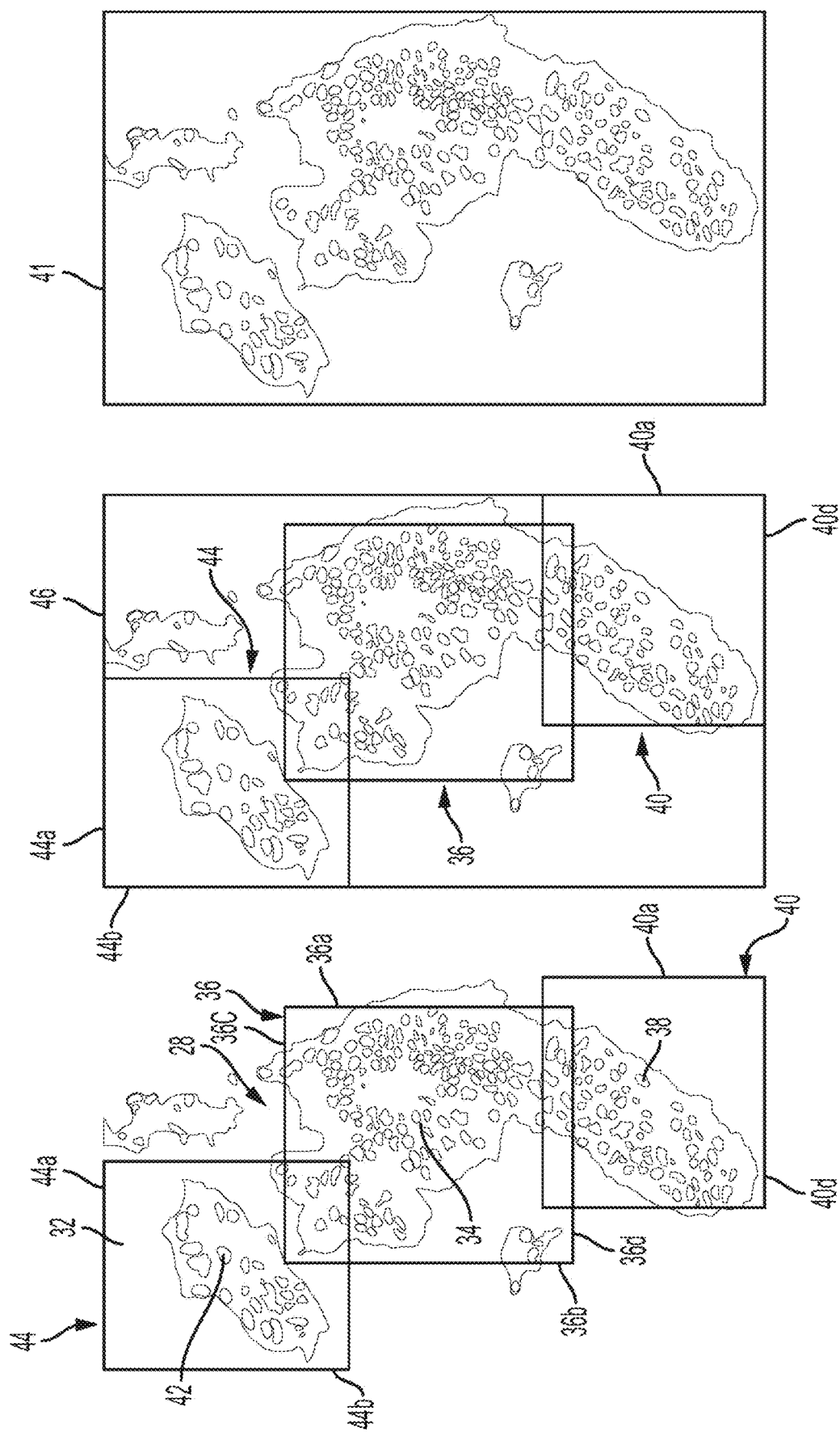
FIG. 3A is a schematic view of a digitized slide area showing three exemplary overlapping envelopes generated by the system in accordance with an exemplary embodiment of the invention.
FIG. 3B is a schematic view of a frame dynamically generated by the system to capture the overlapping envelopes of FIG. 3A.
FIG. 3C is schematic view of a resultant tile formed in accordance with FIGS. 3A and 3B.

FIGS. 3A-3C show exemplary methods for creating a tile from a slide in accordance with embodiments of the invention, where the tile size is derived from the neural network score. Referring to FIG. 3A, a digitized slide area 28 is shown. The slide area 28 contains images of tissue fragments (e.g., 32) formed of individual cells (e.g., 34, 38, 42). In the neural network scoring step, each cell in area 28 may be given a neural network score. For example, cell 34 may be ranked relatively high for abnormality (e.g., 0.75). As a result, the system creates a corresponding large envelope 36 (e.g., 15×15 microns, for example calculated according to the score times a fixed constant, e.g. 20 microns, for the edges of the bounding square) with cell 34 in its exact center or general center. In embodiments, the size of the envelope may be determined with reference to a size of the average cell of the type under examination. For example, in embodiments, if the cell under examination is a cell of average size in diameter of a given number of microns (e.g. 5-10 microns, in the case of esophageal cells), then the envelope dimensions may be determined based on the score and based on a multiple of that average size, for example, the score times 2 or 3 or 4 or 5 or 6 times the average size. In embodiments, the dimensions of the envelope may vary exponentially according to the score, for example, by multiplying the dimension size by a constant base (e.g. 2, 3, 4) raised to the power of the score, or by a sub-one constant base (e.g. 0.5, 0.75) raised to a power of a multiplicative inverse of the score, thus greatly decreasing the dimension size when the score is low relative to the dimension size when the score is large.

In other embodiments, the envelope dimensions may be of a fixed size (e.g. 2 or 3 or 4 or 5 or 6 times the average size), provided that the score exceeds a predetermined threshold (e.g. 0.5 or 0.8). The threshold may be dynamically modified based on whether the resultant false positive or false negative rate, for example as measured by later pathologist evaluation, e.g. using the display methodologies as discussed herein, exceeds a predetermined rate.

By contrast, cell 38 received a lower neural network score because it is morphologically closer to normal, and as a result, the system generates an envelope 40 around cell 38 that is smaller in size than envelope 36.

Cell 42 also exhibited a moderate level of abnormality and, as such, the system generated envelope 44 surrounding cell 42. Envelope 44 is larger than envelope 40 because it has cells that have higher confidence or specificity (i.e., higher neural network score) than the cells in envelope 40. However, as described, envelope 36 is larger than envelope 44 because its cells are more abnormal than the cells in envelope 44.

Each of the respective envelopes may be square or rectangular shapes having right and left borderlines (e.g., 36a, 36b) and top and bottom borderlines (e.g., 36c, 36d). For example, for a rectangular shape, in embodiments the determined height may be multiplied by a fixed value to arrive at a width so as to account for a known aspect ratio of a screen being used by the pathologist (e.g. 16:9 according to one such common aspect ratio). In exemplary embodiments, other shapes may be employed, such as circles surrounding the cells from which the scores are derived (e.g., circles defined by a center point and a radius). As further shown, envelope 44 has an area that overlaps with the top borderline 36c of envelope 36, and envelope 36 has a lower segment that overlaps with an upper segment of envelope 40. It will be understood that envelopes 44, 36 and 40 are relatively large due to the presence of high-ranking cells within each of the envelopes. The presence of high-ranking cells within each of envelopes 44, 36 and 40 causes these three envelopes to be relatively large and accordingly they have overlapping segments. It will further be understood that similar treatment, as discussed herein, in various embodiments, may be afforded or may not be afforded where respective envelopes do not overlap in area but share a common borderline or portion thereof (i.e. the respective envelopes being tangential or adjacent).

In embodiments of the invention, envelope size may be determined by a combination of factors that, in combination, contribute to ensuring that the system captures substantially all the cells that comprise a cluster or grouping of cells. In a slide with millions of cells, and identifying which are neighbors of each cell is a daunting problem. In embodiments, for combining neighboring squares to get a larger square, an r-tree data structure is preferably used for speed purposes. Cells that are grouped (e.g., in a cell cluster) tend to be positioned closer to one another than cells that are unrelated to the group. The system takes these spatial tendencies into account to ensure that envelopes are adequately sized to encompass a grouping of cells with a high degree of confidence that the grouping is presented within the envelope. In an exemplary embodiment, the size of an envelope is not derived directly or solely from the neural network score, but rather the neural network score may be further modified. For example, in embodiments of the invention, the neural network score may be multiplied by a dynamically generated multiplier, for example, one based on distance between cells. For example, in embodiments of the invention, the multiplier may be derived by calculating an average distance between respective cell nuclei for a given sample or sample area (e.g. an area defined according to an area determination made according to the neural network score before the multiplication) and then multiplying the average distance by a number (e.g., two, three or more). Thus, if the average distance between cell nuclei is multiplied by two, then the multiplier will present double the distance between cells. In other embodiments, the multiplier, or an additional multiplier, may be based on the classification. For example, a first type of presumed cellular abnormality generally associated with tight cell groupings may have an associated multiplier of less than 1, such as 0.7, while a second type of cellular abnormality generally associated with disparate cell groupings may have an associated multiplier of greater than 1, such as 1.5. In embodiments of the invention, a neural network score is multiplied by the multiplier or multipliers to yield a final product. The final product is then converted to units of distance to form envelopes. The particular multipliers may be set or reset so as to encompass an influence region generally or usually surrounding features of relevance that tend to occur around a given point, e.g., a cell of interest. If an average distance between cell nuclei is determined for the sample of, e.g., 0.5 average cell widths for the cell types of interest, then an influence region is set, e.g., 0.5 to 1.5 of such cell widths, in which cells falling within this area are considered within the region of influence. This can be repeated for each cell to determine an entire region of influence. Cells falling, e.g., at value 2.0 of such cell widths from a cell, may be considered outside the region of influence.

The multiplier set forth in embodiments of the invention helps to ensure that tiles are adequately sized and that there is a high degree of confidence that respective cells of a grouping of cells are included. In this regard, for example, if cells are tightly bunched together and, thus, the distance between respective nuclei is small, then a small multiplier is used. However, if cells are more loosely associated and are located farther apart from each other, then a larger multiplier will be generated to yield a larger envelope size in order to ensure that enough representative cells are yielded. A feedback mechanism may be introduced, for example feedback provided by one or more pathologists using the inventive system, of whether envelopes shown are too large or too small, and such feedback may be used to adjust or dynamically adjust the tile sizes or multipliers employed. A neural may also provide such feedback, for example by being trained with images of cell clusters of optimal and suboptimal sizes, tagged with indications of whether the multiplier should be increased (as in the case of images that do not contain the entire cluster), decreased (as in the case of images that contain much more than an entire cluster), or maintained (as in the case of images appropriately showing an entire cluster).

In embodiments of the invention, once envelopes are generated, the system then detects envelopes that contain overlapping, or, in some embodiments, adjacent, areas (step 56, FIG. 2) and generates a tile that is sized and shaped to incorporate all contiguous overlapping envelopes, for example, as shown in FIG. 3B. Specifically, the system dynamically generates a frame 46 that is sized and shaped to capture envelopes 44, 36 and 40. As shown in FIG. 3B, in order to capture envelopes 44, 36 and 40 in one tile, in an embodiment, frame 46 is formed that is large enough to incorporate the highest point as defined by top borderline 44a of envelope 44, the lowest point defined by bottom borderline 40d of envelope 40, the left most point defined by left borderline 44b of envelope 44, and the right most point defined by right borderline 40a of envelope 40, in the manner of a smallest bounding rectangle. In other embodiments, the rectangle may be formed so as to contain the boxes while maintaining a particular aspect ratio, such a ratio associated with an electronic display of the pathologist (e.g., 16:9). In other embodiments, the frame 46 may be formed, potentially as other than a rectangle, so as to consist only of, or be based on, its combined shapes. For example, two rectangles sharing an area around their corners may be combined into a concave octagon frame. An R-tree may be used for merging of rectangles. Or two overlapping circles may be combined into a larger circle or oval or other shape bounding such constituent circles. An existence of an overlap between two circles may be determined for example according to whether the distance between their centers is less than (or in some embodiments where adjacency rather than overlap is sufficient, less than or equal to) the sum of their radii. Use of squares and rectangles however, may advantageously save on computational resources, for example with respect to the reformation of such envelopes or tiles into larger tiles. Such more complicated or larger frames may be stored along with its corresponding bounding rectangle or other frame, such that the views pertaining to each may optionally be selected or presented, for example according to particular display software or according to particular selections of the pathologist using the program.

FIG. 3C shows a resultant tile 41 that is formed (step S7, FIG. 2) and will be displayed, for example as part of a series of tiles that represent the whole slide, or parts of the side determined to be of suitable diagnostic relevance, in accordance with various embodiments of the invention.

In embodiments of the invention, the system is configured to apply threshold criteria in determining whether or not to merge overlapping envelopes. For example, in embodiments of the invention, the system only merges envelopes having cells with neural network scores above a certain threshold. In embodiments of the invention, overlapping envelopes are merged when the neural network score is at least 0.6, or is at least 0.7, or is at least 0.8. Thus, in embodiments of the invention, the system does not blindly merge overlapping envelopes, but rather it applies these criteria to ensure that the envelope to be merged contains diagnostically important information.

Thus, in embodiments, in order to identify "bad" cells, e.g., malignant cells, clusters may be built using the influence region process of determining overlap, but a neural network score and/or classifier result may be used to ascribe a confidence score to the cell which is determined as overlapping. For example, a confidence score may be applied, where cells displaying pathological archetypes as determined by the neural network (for example, one trained with images of pathological and non-pathological cell clusters each tagged with whether or not they are pathological or probabilistic scores based on a probability of such being pathological) may be given a confidence score of up to 1.0, and normal cells a score of down to 0. In embodiments, the confidence score may be used as a multiplier of the distance establishing whether the cell or determined region will be considered overlapping with a nearby cell or determined region—with healthy normal cells or regions based thereon having a zero multiplier thus being excluded. In embodiments, this results in merging, into the displayed field or region, occurring as a function of both nearness of cells and regions and of apparent pathological-ness of such cells/regions. Thus, the locations and proximity to one another of "bad" or potentially "bad" cells (e.g., malignant, dysplastic, etc.) are taken into account in the final displayed tiles, including merging. In exemplary embodiments, the type of classification (e.g. potentially cancerous, potentially dysplastic, etc.) may also be taken into account as a multiplier in the merging determination. Ultimately, in embodiments, the bin-packing or other presentation on an electronic display shown to the pathologist may put, for example subject to readability and available screen space constraints, as much important information for the user, e.g., a pathologist, into the given display as possible. For example, the most important region may be displayed at a legible size within a display, along with the next most important region, and so on, until it is not possible to add additional regions to the screen. The displayed results may be weighted or emphasized or sorted, e.g., by size or by a combined or averaged score of constituent envelopes pertaining to constituent cells, or by confidence. A linear display, with the largest most important tile information on the left hand side and then progressing linearly to smaller tile size/less important information to right is one embodiment. Advantageously, in embodiments, this can result in temporal decrease in assessment times needed to make an identification or diagnosis versus conventional techniques of $5x$ or more.

Notably, in embodiments, where an envelope generated by the system does not overlap with or contact a neighboring envelope, then that envelope may be rendered by itself as a tile. For example, with reference to FIG. 3A, if envelope 44 did not overlap or contact envelope 36, for example because its constituent cells happened to be located significantly further up and/or to the left, then envelope 44 could be rendered as its own tile (and would not include the cells in envelope 36) and could be smaller than tiles made from overlapping envelopes (e.g. a tile made from the combination of envelopes 36 and 40).

Figure 4:
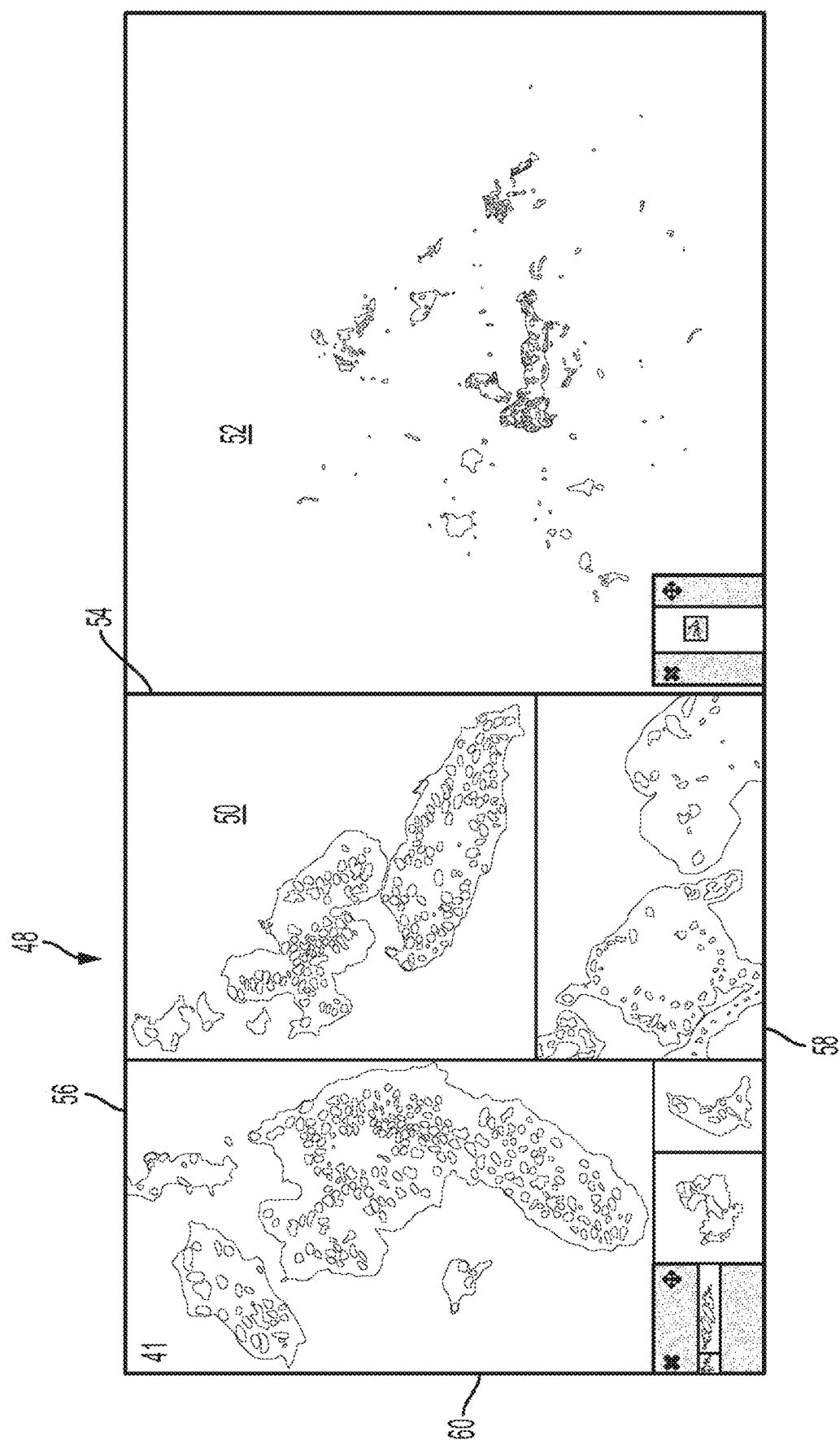
FIG. 4 is a schematic view of a display screen showing a series of tiles on one side of a split screen and a zoomed-out view of a whole digitized slide on a second side of a split screen in accordance with exemplary embodiments of the invention.

FIG. 4 shows a display screen 48 according to embodiments of the invention that displays the tiles generated by the software of the present invention. As shown, display 48 is divided into a left viewing pane 50 and a right display pane 52. In embodiments, panes 50, 52 may be separated by dividing line 54. As shown, viewing pane 50 has an upper boundary line 56, a lower boundary line 58, a left boundary line 60 and a right boundary line (which may be dividing line 54, for example as shown). In embodiments of the invention, left viewing pane 50 displays tiles in accordance with an embodiment of the invention, and right pane 52 displays a digitized image of the whole slide. In embodiments, images displayed in each of panes 50, 52 can be panned and zoomed by clicking on or within the image or using a mouse scroll wheel or by another tool or tools built in or integrated with the viewing software or display screen.

In embodiments of the invention, tiles displayed on the left pane 50 are confined in the y direction between the upper boundary line 56 and the lower boundary line 58. In embodiments, tiles may only be scrolled, in the y direction (or in other embodiments, only in the x direction). In embodiments, scrolling or movement may occur in a different direction (e.g. also in the x direction, or in other embodiments, also in the y direction), but subject to the image automatically snapping or otherwise reverting back to a view comprising the area between the boundary lines, (for example, when a mouse button used for movement is released) so as to ensure that all relevant imagery will ultimately appear on the screen of the pathologist once the pathologist completes scrolling in the y direction. In embodiments, the snapping or reverting back requires input by the pathologist (e.g. a mouse click), but is required before additional scrolling in the main direction may occur. Thus, customizability of view and completeness of review may advantageously be achieved. Additionally and advantageously, in embodiments, tiles may be presented in a linear continuum, from areas of highest diagnostic significance (e.g., large tiles or tiles otherwise associated with high confidence scores or combined scores or important types of classifications) to tiles of least diagnostic significance (e.g., smaller tiles, or tiles otherwise associated with lower confidence scores or less important types of classifications).

Since, in embodiments, the larger tiles may include the most diagnostically significant information (groups of concerning cells), a pathologist can review the large tiles first and may be able to make a quick and accurate diagnosis, for example in the event that the initial tiles of highest diagnostic significance immediately confirm the "bad" (e.g. malignant) result for which the pathology review was commissioned. In embodiments, the smaller tiles may be reviewed later in the process, since such tiles may be less likely to (or do not) include any concerning cells.

In this regard, as mentioned, tiles that include overlapping envelopes will often tend to be larger than the tiles formed of a singular envelope. In embodiments of the invention, a bin packing algorithm is employed to preferentially pack generated tiles in descending order of size, from largest (most diagnostically significant) to smallest (least diagnostically significant). This places the largest tiles first along a linear presentation and the less important tiles are presented toward the tail end of the linear presentation.

In embodiments, bin packing algorithms employed may be 2-dimensional bin packing algorithms, such as one-phase algorithms, two-phase algorithms, hybrid first-fit, hybrid-next fit, hybrid fest-fit, floor-ceiling, finite next-fit, finite first-fit, finite bottom-left, next bottom-left, alternate directions 2-dimensional bin-packing algorithms, and rectpack. In embodiments, larger tiles may be placed first, and then smaller tiles may be placed between the larger tiles, space permitting.

Other or additional organizations may be employed in embodiments, for example, the slides may be sorted into separate sets (e.g. each pertaining to an individual classification), so that review for different conditions may be sequentially performed by the pathologist or performed in an order of the pathologists or the programming of the software's choosing. In embodiments, the tiles may be presented linearly (e.g. in a row, with no tile presented on top of another tile) for review, rather than packed into a 2-dimensional space.

Figure 6:
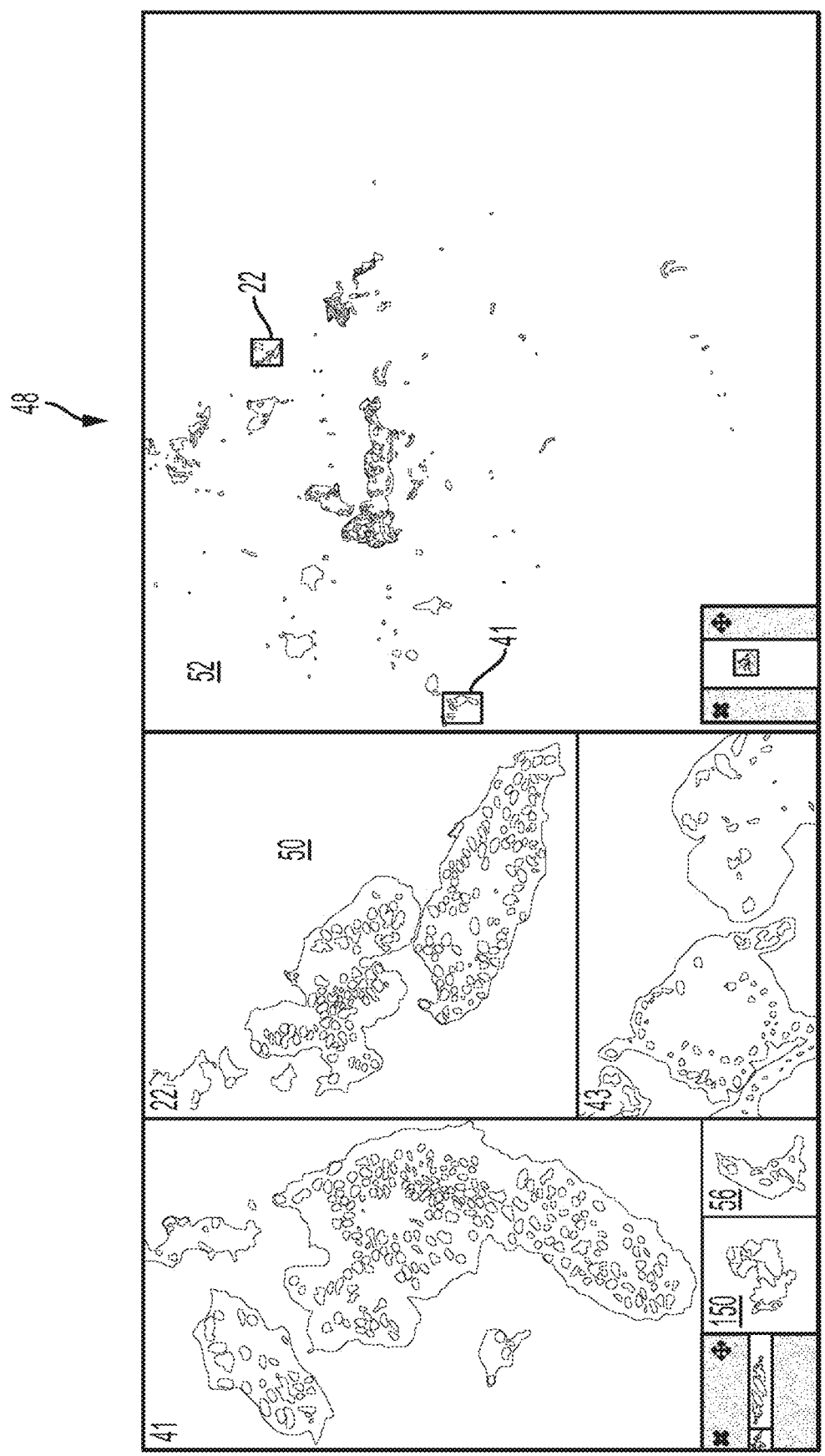
FIG. 6 is a schematic view of a display screen showing a series of tiles in a first side of a split screen and two respective tagged areas in the zoomed-out view of a whole digitized slide shown in a second side of a split screen in accordance with exemplary embodiments of the invention.
Figure 7:
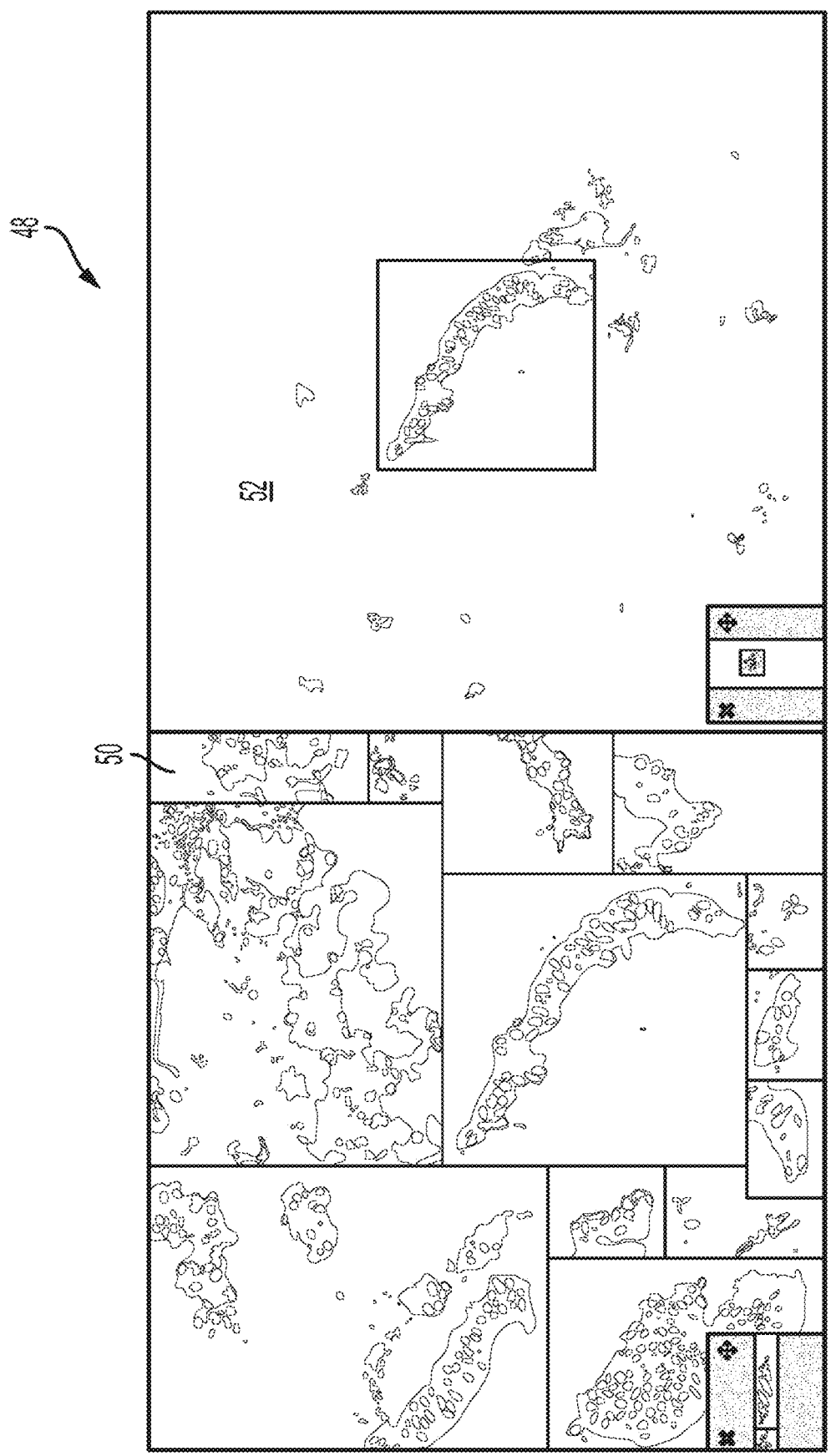
FIG. 7 is a schematic view of a display screen showing a series of tiles in a first side of a split screen and whereby the tiles are generally smaller than the tiles shown in FIG. 6 in accordance with embodiments of the invention.
Figure 8:
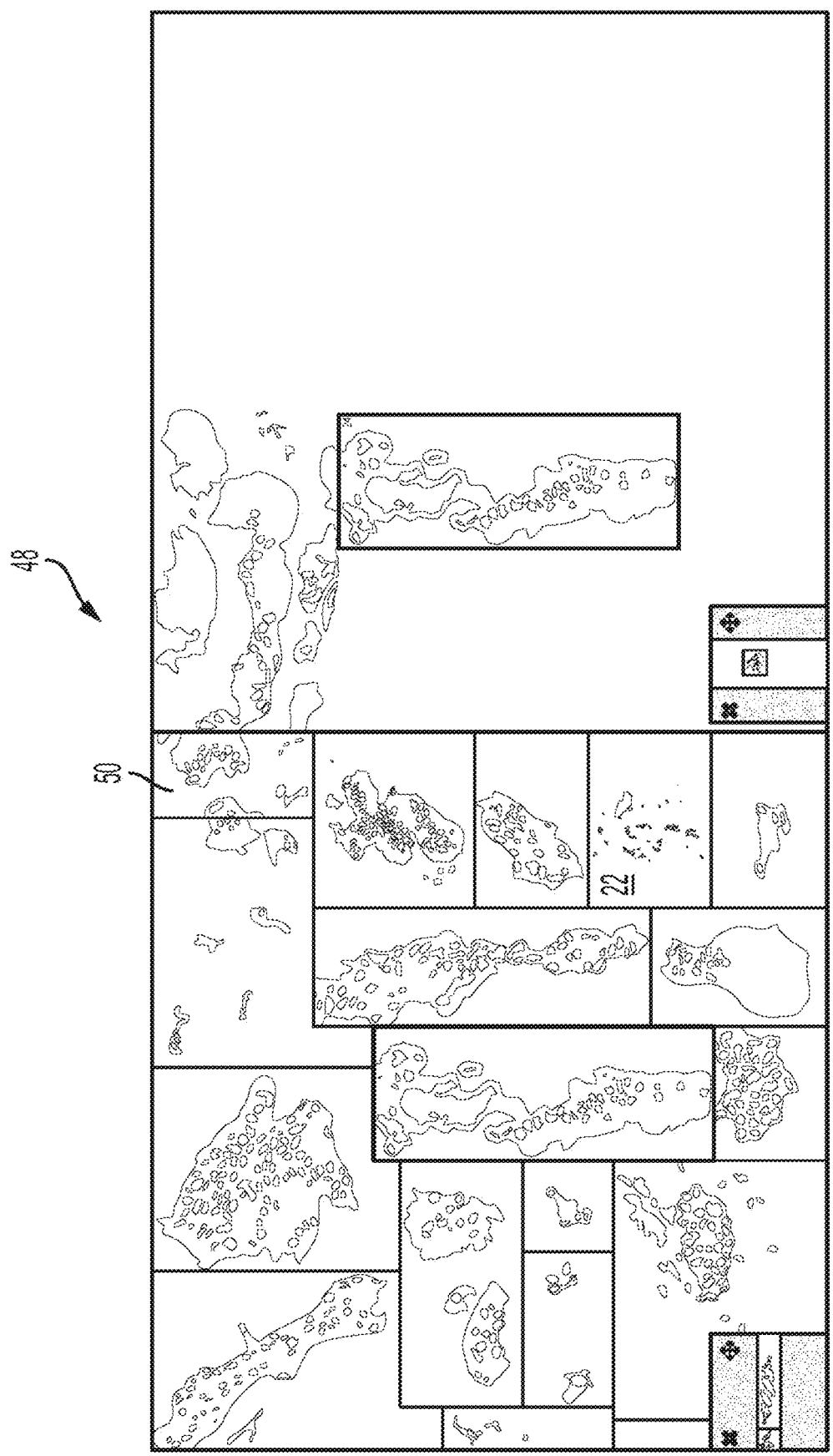
FIG. 8 is a schematic view of a display screen showing a series of tiles in a first side of a split screen and whereby the tiles are generally smaller than the tiles shown in FIG. 7 in accordance with embodiments of the invention.
Figure 9:
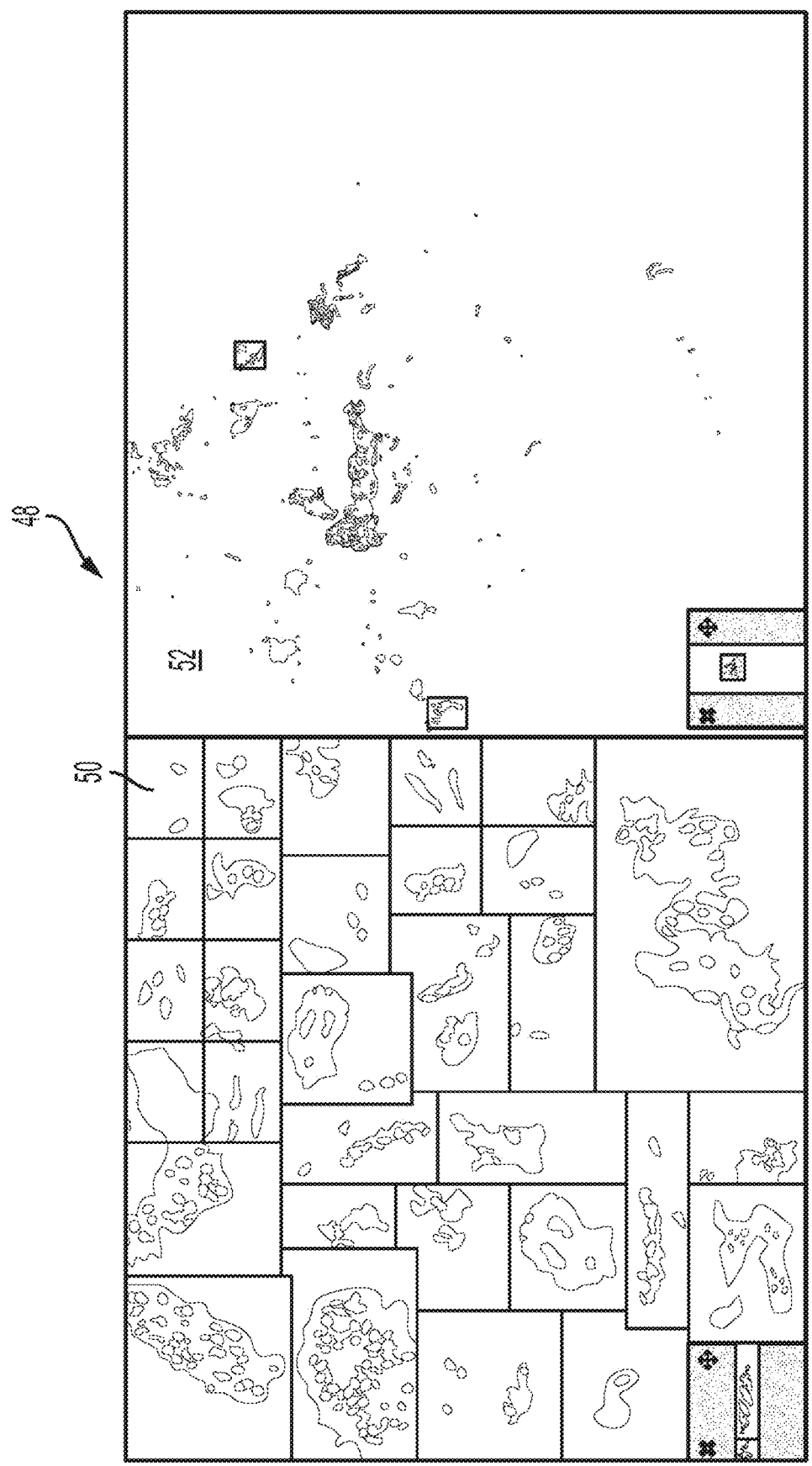
FIG. 9 is a schematic view of a display screen showing a series of tiles in a first side of a split screen and whereby the tiles are generally smaller than the tiles shown in FIG. 8 in accordance with embodiments of the invention.
Figure 10:
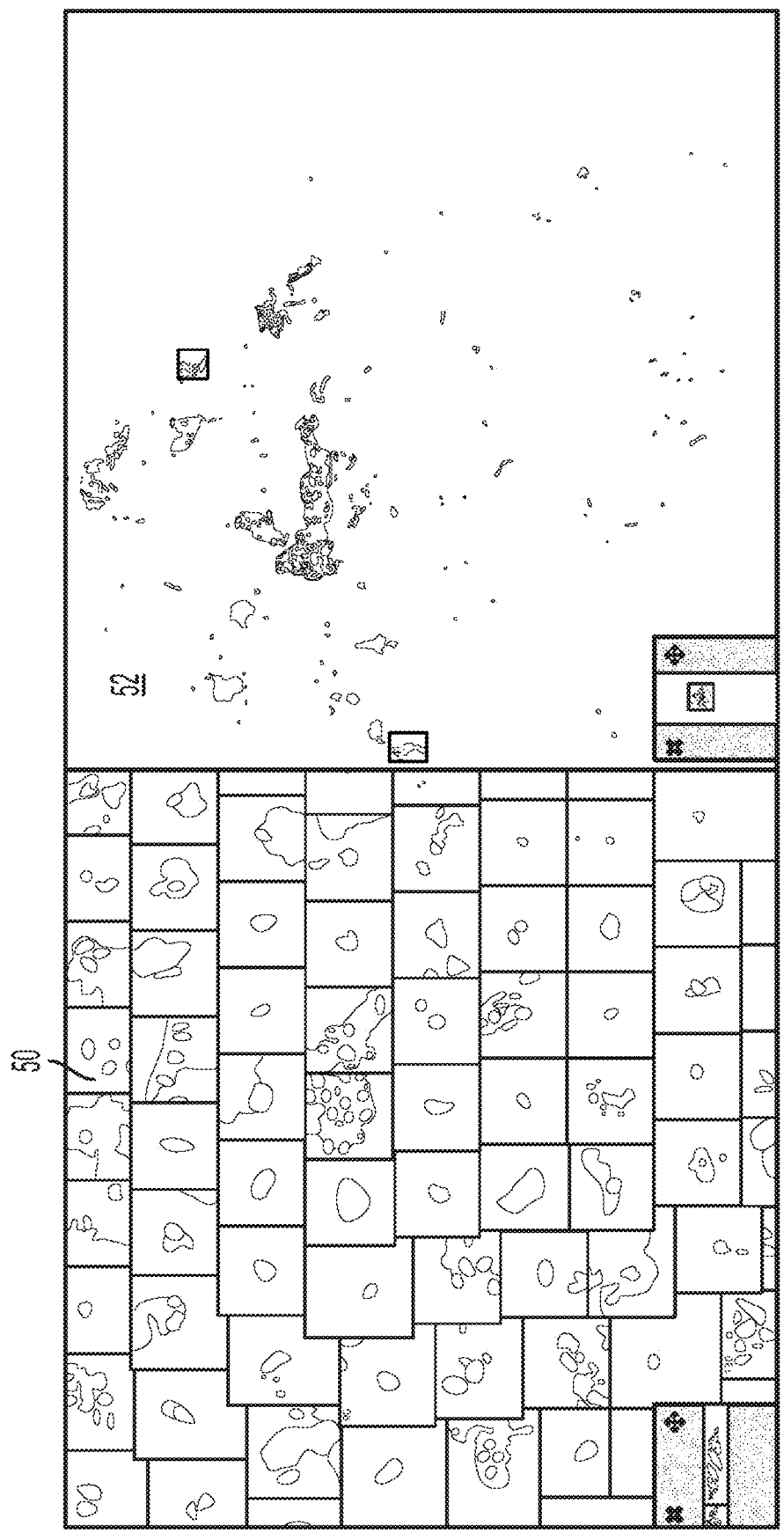
FIG. 10 is a schematic view of a display screen showing a series of tiles in a first side of a split screen and whereby the tiles are generally smaller than the tiles shown in FIG. 9 in accordance with embodiments of the invention.

For example, with reference to FIGS. 6-10, successive screens 48 are shown demonstrating respective views of viewing pane 50 as a user scrolls in the y direction (e.g., from right to left). In other embodiments, the scrolling may occur from top to bottom (e.g., in the x direction), or from right to left, or from bottom to top. As shown, there are few large tiles in pane 50 of FIG. 6. These tiles may represent the most diagnostically significant information in the specimen. In FIG. 7 the tiles are generally smaller in size than those of FIG. 6. As the tiles continue in the y direction, and with reference to FIGS. 8 and 9, the tiles gradually become smaller in size. FIG. 10 represents tiles presented at the tail end of the series. Notably, whereas, the tiles of FIGS. 6-9 contain tissue fragments and cell clusters, the tiles shown in FIG. 10 predominantly contain single cells, which as described, may offer the least amount of clustered diagnostic information.

In embodiments, a pathologist may review the largest tiles (here, in FIG. 6) first, and may spend the most time reviewing these tiles, since they may include the most diagnostically significant information. In the absence of the present invention, the pathologist would not know where to start reviewing cells on a slide, and therefore, choose a random area to start with. Thus, as is often the case, the pathologist may often, using prior computer-implemented and non-computer-implemented review tools, through guesswork, start with the least diagnostically important area on the slide and spend significant time seek out more important areas.

Once the pathologist completes his or her review of the tiles in FIG. 6, he or she may move on to the next series of tiles in FIG. 7, since they are the next most diagnostically significant. The pathologist may then progress through the tiles in FIGS. 8-10, spending less and less time on each series of tiles as they get smaller and smaller. This is because as tiles get smaller, they may have less diagnostically significant information.

By including the most diagnostically significant information in the largest tiles, and by organizing the tiles from largest to smallest, the pathologist is guided to start with (and spend the most time reviewing) the most diagnostically significant information. This solves a significant problem that pathologists face with known manual and computerized review methods. Indeed, under the prior art, a pathologist would haphazardly guess where on the slide to begin, and would often spend too much time on areas of the slide that were insignificant for diagnostic purposes.

Moreover, since the largest tiles group together the most diagnostically significant cells, it is much more likely that the pathologist will be able to make a more accurate diagnosis as compared to prior diagnostic methods, which required the pathologist to first find cells of concern and then map their location relative to neighboring cells of concern. The prior methods are not only cumbersome, but prone to significant human error.

Figure 5:
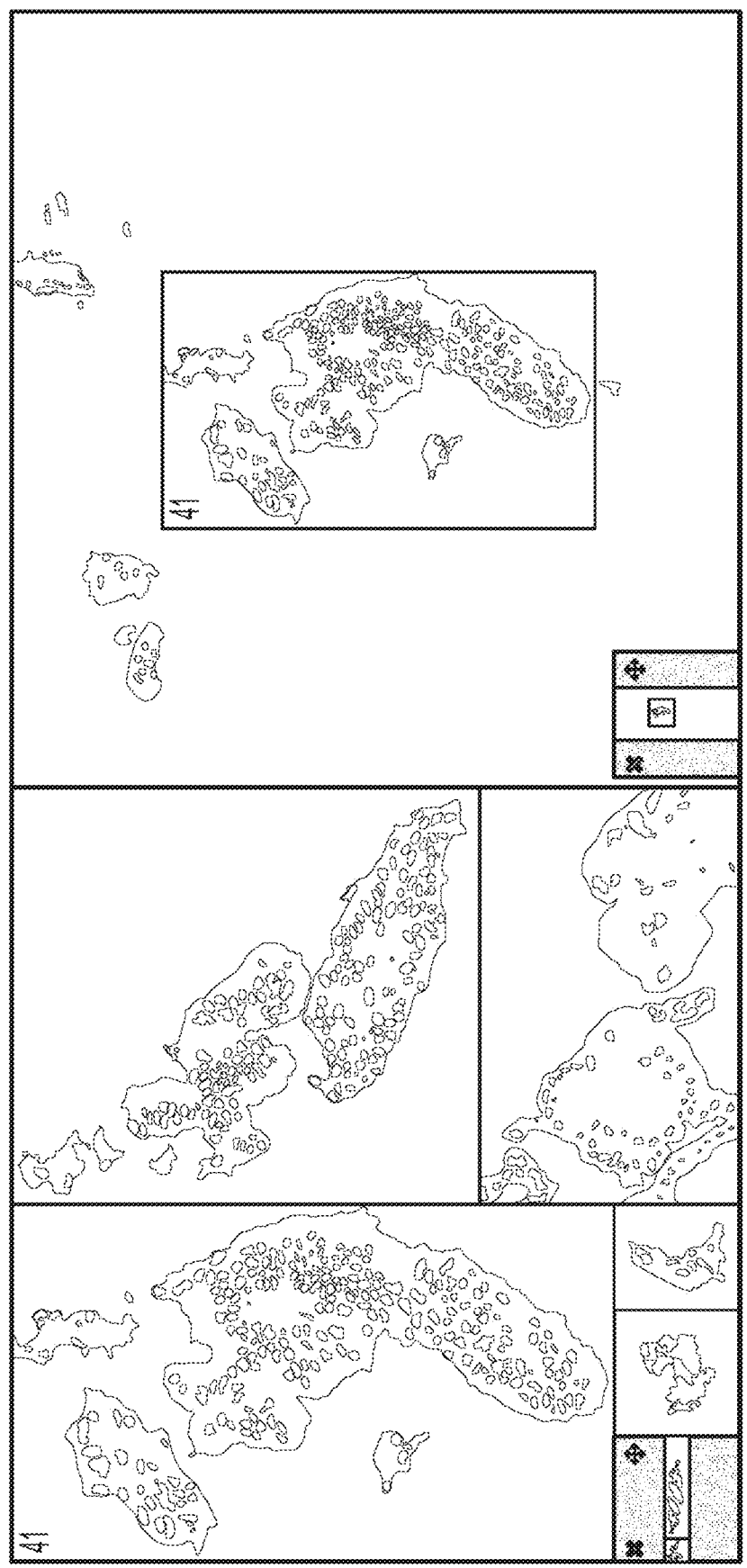
FIG. 5 is a schematic view of a display screen showing a series of tiles in a first side of a split screen and a zoomed-in view of the area from which the tile was derived on the whole digitized slide in a second side of the split screen in accordance with exemplary embodiments of the invention.

In embodiments of the invention tiles displayed in the left viewing pane 50 are mapped to the right viewing pane 52. In this regard, a user may select a tile in viewing pane 50 and it will be displayed in context of the full digitized slide in right viewing pane 52. For example, FIG. 4 shows a group of tiles in left viewing pane 50. Right viewing pane 52 shows a zoomed-out view of the entire digitized slide. In embodiments, if a user wishes, for example, to see where the information of tile 41 is found within the context of the digitized slide, the user may select tile 41, and as shown in FIG. 5, the right viewing pane 52 will zoom into the region of the slide from where tile 41 is derived. In embodiments, the user may then zoom out to see neighboring regions or, alternatively, the user may zoom in to see cells of interest in greater detail. This may allow the pathologist to easily keep track of where the cells being examined (e.g., the tiles in viewing pane 50) are located relative to all of the information on the slide (which is shown in viewing pane 52). This marks a significant improvement over prior manual and computerized methods since the pathologist would, in the prior art, need to manually map the location of cells of interest on a slide. In embodiments of the invention, displayed versions of slide portions may be based on compressed image data, for example, when the tile is shown in a zoomed out or relatively zoomed out view. Advantageously, the amount of required data transmission may thereby be reduced, as the entirety of the data available with respect to the image need not be transmitted to the displayed computer. In some embodiments, the total size of an uncompressed slide may approach, for example, 20 gigabytes, and thus significant time and data transfer savings may occur by avoiding the need to simultaneously present an entire uncompressed slide image to a pathologist. In embodiments, the uncompressed slide image may be streamed to the pathologist's display during the review process, so as to allow initial review prior to receipt of the entire uncompressed image. The streaming may occur with respect to tiles of the slide in the order they are to be presented to the pathologist, so as to further avoid delay, as the streaming for later tiles to be presented may be downloaded while the pathologist reviews earlier, e.g. more important, tiles. If the user zooms in closer, additional data may be provided to the users computer, so as to enable the relevant portion of the image to be displayed in the tile as-zoomed in to be shown in an appropriate resolution for review. Advantageously, the pathologist viewing the display may thereby be able to view, for example, details pertaining to the nucleus of a cell sufficient for diagnosis when in such a zoomed in view. In embodiments, different tiles may be separately zoomed in and out by the pathologist so as to provide for customization in the pathologist's review of the slide image.

With reference to FIG. 6, in other embodiments of the invention, the system allows a user to view the relationship of two different tiles in the context of the larger whole slide image. For example, as shown, a user may select tiles 41 and 22, and the slide areas from which each of these tiles are derived are highlighted on right viewing pane 52.

Figure 11:
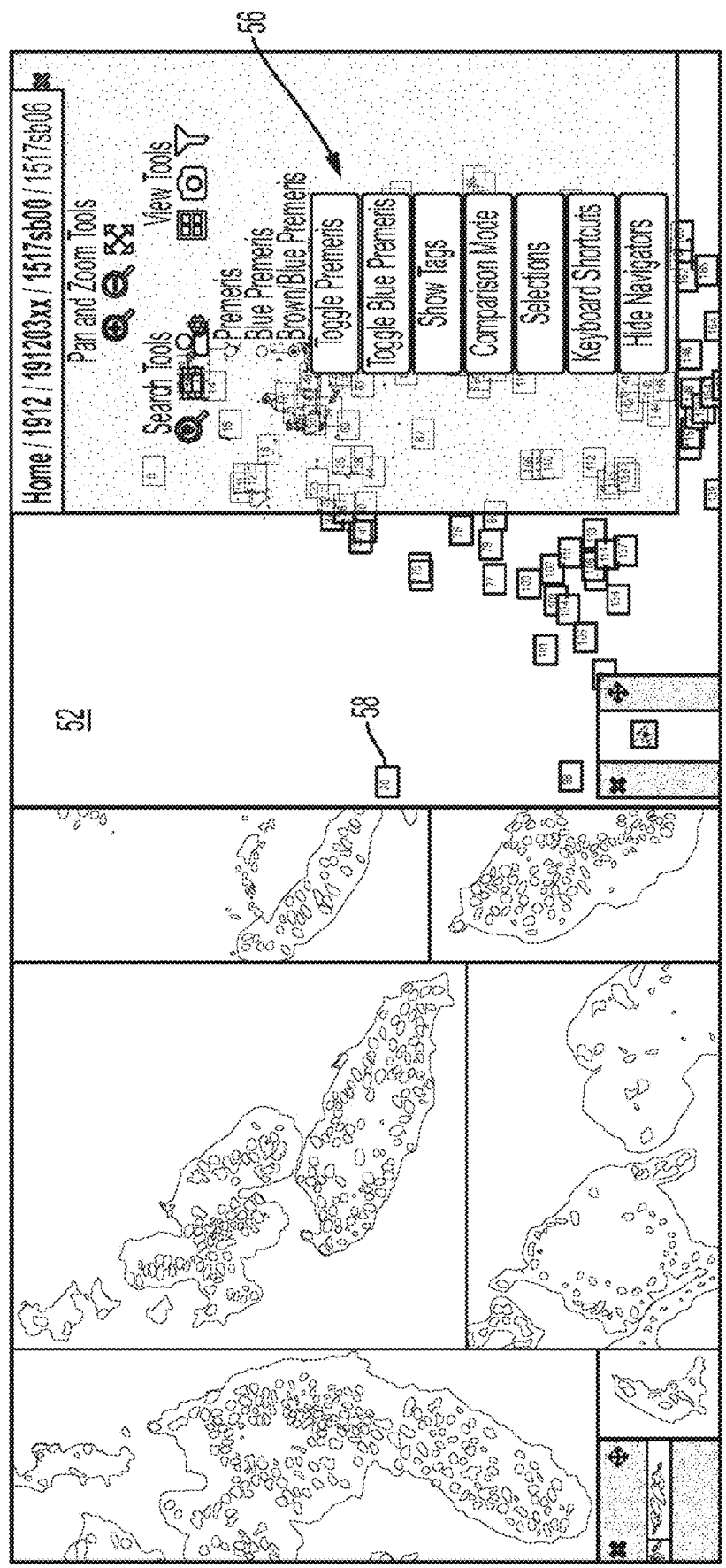
FIG. 11 is a schematic view of a display screen showing a viewing pane where tissue areas that have stained positive for an immunohistochemical stain(s) are tagged by the system in accordance with embodiments of the invention.

With reference to FIG. 11, in embodiments, the system may be configured to mark portions of a digitized slide (e.g., with a flag) that have previously been identified by the computer as "positive" for abnormality, and/or portions that have been identified as "negative" for abnormality. The system is configured to present information relating to positive and negative regions in any of various configurations. This feature enables the pathologist to easily "jump back" to cells of diagnostic significance as he or she reviews a slide. In embodiments, other markings may be made available for presentation to the pathologist, for example, markings pertaining to particularly highly-scored areas, markings afforded particular classifications, and markings of combined tiles and/or of their component parts, and markings pertaining to such other determinations as are discussed herein as being made by the computerized system and/or neural networks.

For example, in one embodiment, the system provides a toolbar or similar menu 56 that allows a user to select actions to output certain views and toggle between various views. In one example, a user may select to display all "positive" areas on a digitized slide. As shown in FIG. 11, upon selection by a user to display positive areas on a slide, the system displays a mark on such slide areas, for example, in the form of a square 58 or other image marker. A user may click on any of the squares (e.g., 58) to enlarge the image of a marked positive area. In embodiments of the invention, marks identifying positive areas may be of a first or different color or visual disambiguation (e.g., red or flashing or shown in broken line, to name a few).

Figure 12:
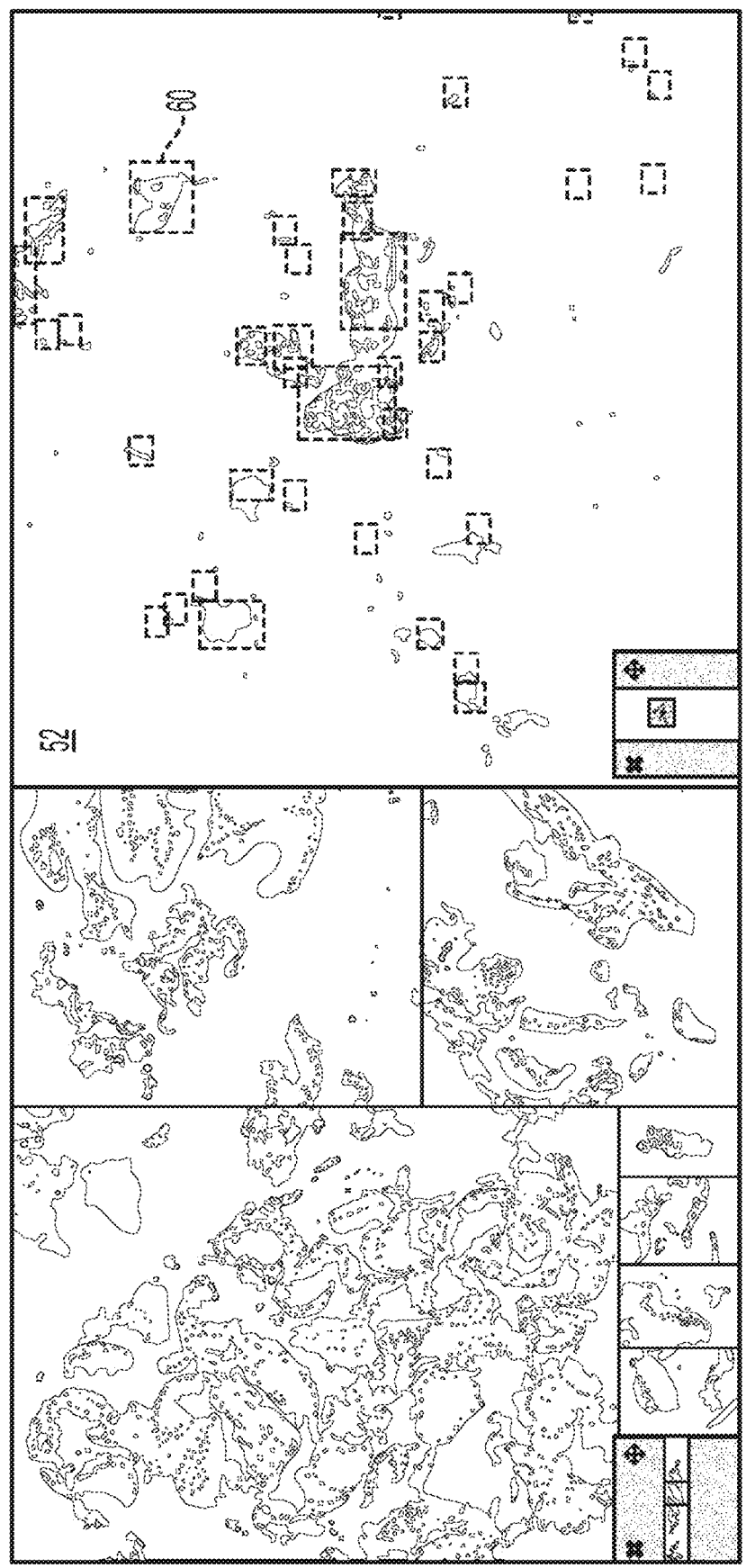
FIG. 12 is a schematic view of a display screen showing a viewing pane where tissue areas that are immunohistochemically negative are tagged by the system in accordance with embodiments of the invention.

In embodiments of the invention, the system is similarly configured to mark portions of a digitized slide that are "negative" for abnormality. For example, with reference to FIG. 12, a user may select (e.g., from an option on menu 56) to mark areas of a digitized slide that are "negative," whereby upon such selection, the system displays a mark on negative slide areas, for example, in the form of a square 60 or other image marker. A user may click on any of the squares (e.g., 60) to enlarge the image of a negative area. In embodiments of the invention, marks identifying negative areas are of a second color (e.g., blue).

Figure 13:
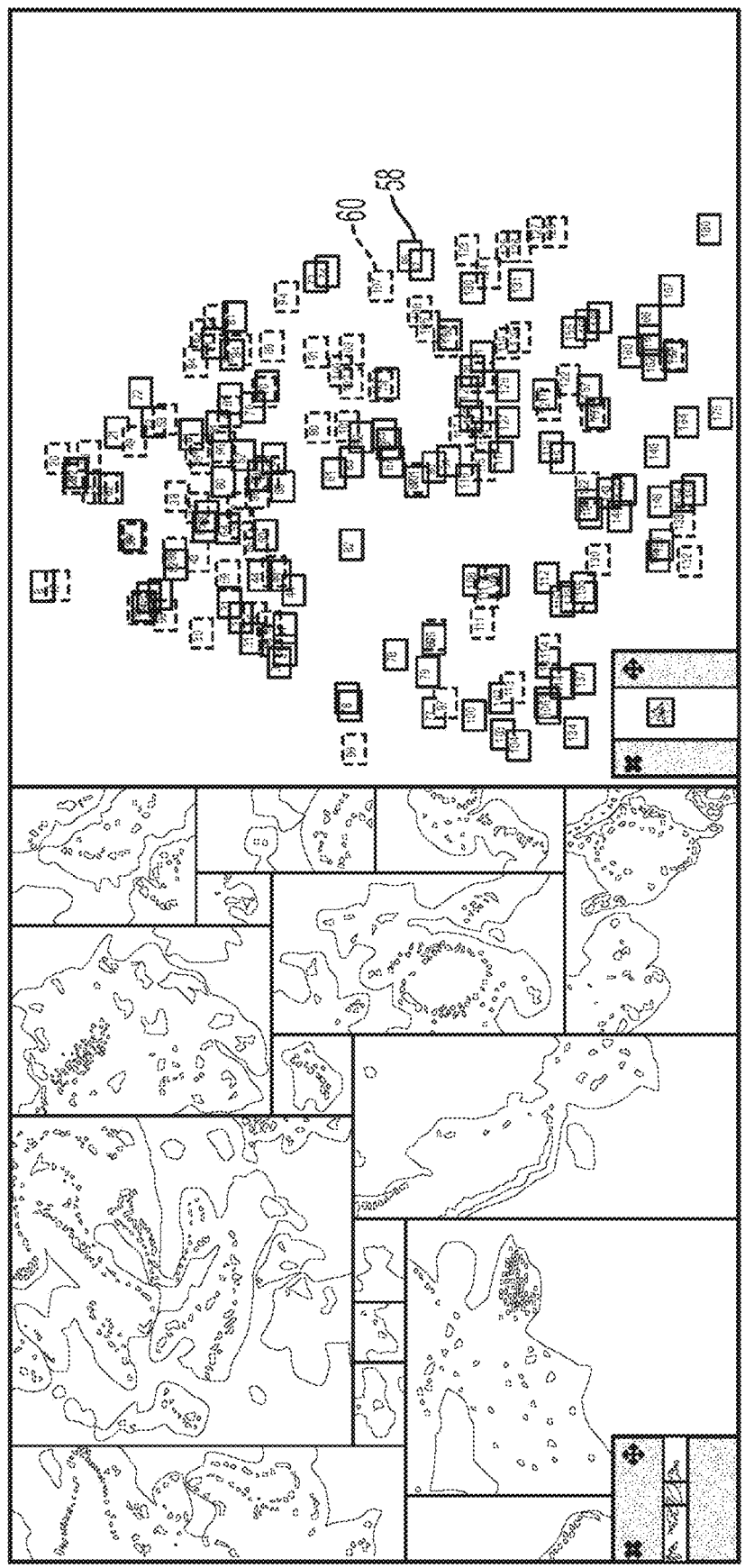
FIG. 13 is a schematic view of a display screen showing a viewing pane where tissue areas that are respectively, immunohistochemically positive and negative are tagged by the system in accordance with embodiments of the invention.

In embodiments of the invention, a user may toggle markers to be displayed on the screen or the user may select an option to display, both, positive markers (e.g., 58) and negative markers (e.g., 60) simultaneously. For example, as shown in FIG. 13 the digitized image of a sample is provided with positive and negative markers marking respective positive and negative slide areas (e.g., 28, 60).

It will be understood that "positive" and "negative" areas may be determined by any of various techniques in different embodiments of the invention. For example, when analyzing glandular epithelium such as tissue obtained from the upper gastrointestinal tract, a stain (e.g., cdx2) is commonly used that binds to abnormal columnar cells and stains such abnormal cells with a certain color (e.g., brown). The system then is able to identify columnar cells that are abnormal by searching for the stain color of interest (e.g., brown). In order to identify unstained (i.e., negative) columnar cells, the system using image-recognition systems such as classifiers and/or trained neural network computers, identifies columnar cells based on morphological characteristics. The system, thus stores information relating stained areas (obtained via color analysis) and information relating to unstained columnar cells (e.g., obtained via computer image analysis).

For example, in embodiments of the invention, the system is configured to visually present a ratio of positive to negative areas on a slide and calculate percentage values based on the spatial relationship. In embodiments of the invention, the system queries the digitized image (or a database containing information based on the digitized image) for all positive and negative areas of the digitized slide. The system then assembles the respective positive areas and presents them in a first area of a display. The system similarly assembles the respective negative areas and presents them in a second area of a display, alongside or proximate to the first area in a manner such that a reviewer may observe the universe of positive areas vis a vis the universe of negative areas.

Figure 14:
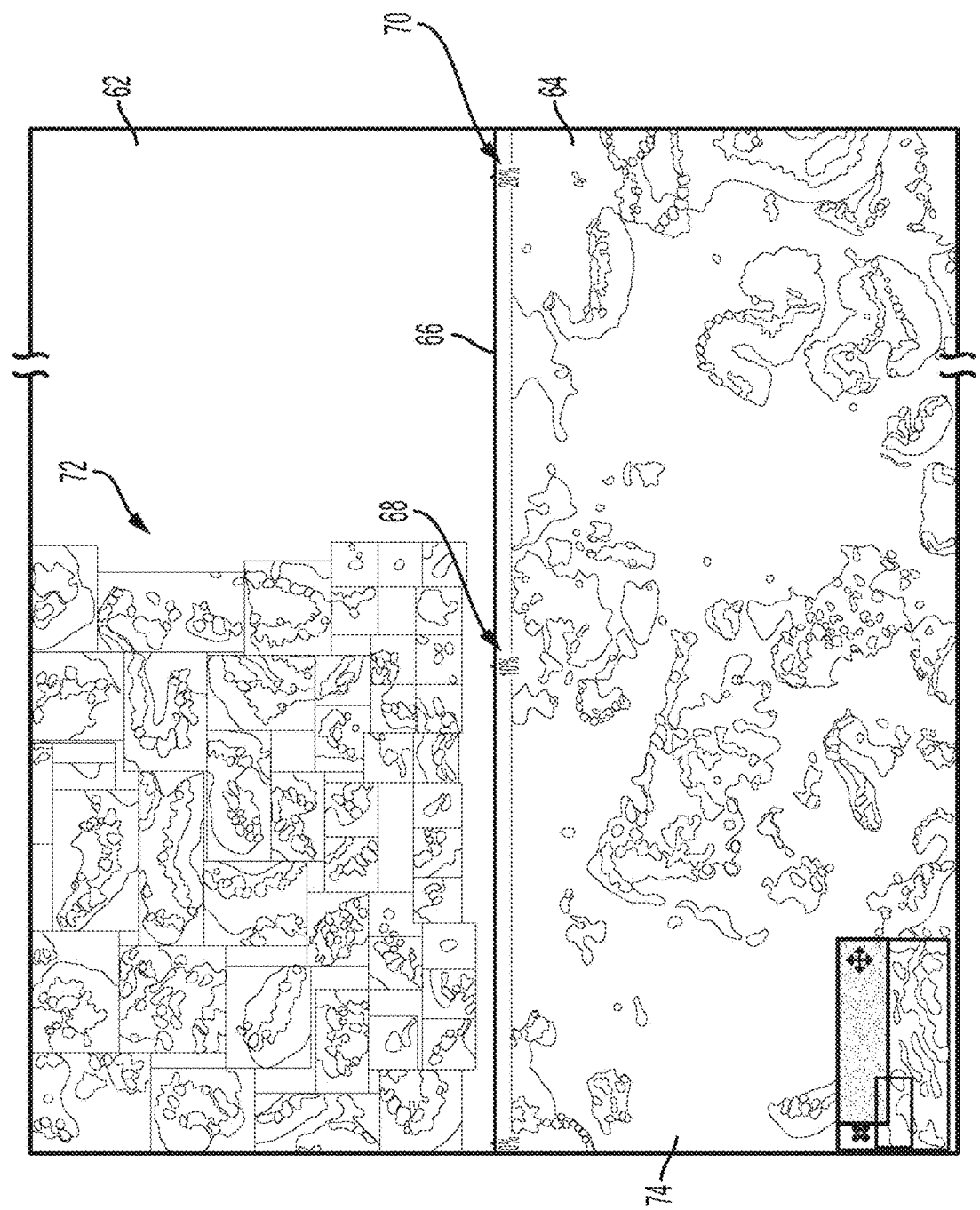
FIG. 14 is a schematic view of a display screen showing an upper viewing pane presenting positive specimen areas and a lower viewing pane presenting negative specimen areas in accordance with embodiments of the invention.

For example, with reference to FIG. 14, a display screen is shown having, according to embodiments of the invention, an upper viewing pane 62 and a lower viewing pane 64. There may be a dividing line 66 separating upper and lower viewing panes 62, 64. As shown, dividing line 66 is provided with markers identifying the percentage values of the slide along a continuum. For example, a 10% marker 68 and an equally spaced 20% marker 70 is shown on dividing line 66. It will be understood that only about 20% of the negative universe is shown in FIG. 14, the entirety (i.e., until 100%) of the negative area may be observed by scrolling to the right. As shown, the aggregation of positive cells 72 spatially represents approximately 12% of the aggregation of negative cells 74 (i.e., occupies significantly less space along an x axis as compared to the negative areas). This provides a pathologist with a visual representation of how positive a specimen may be.

Figure 15:
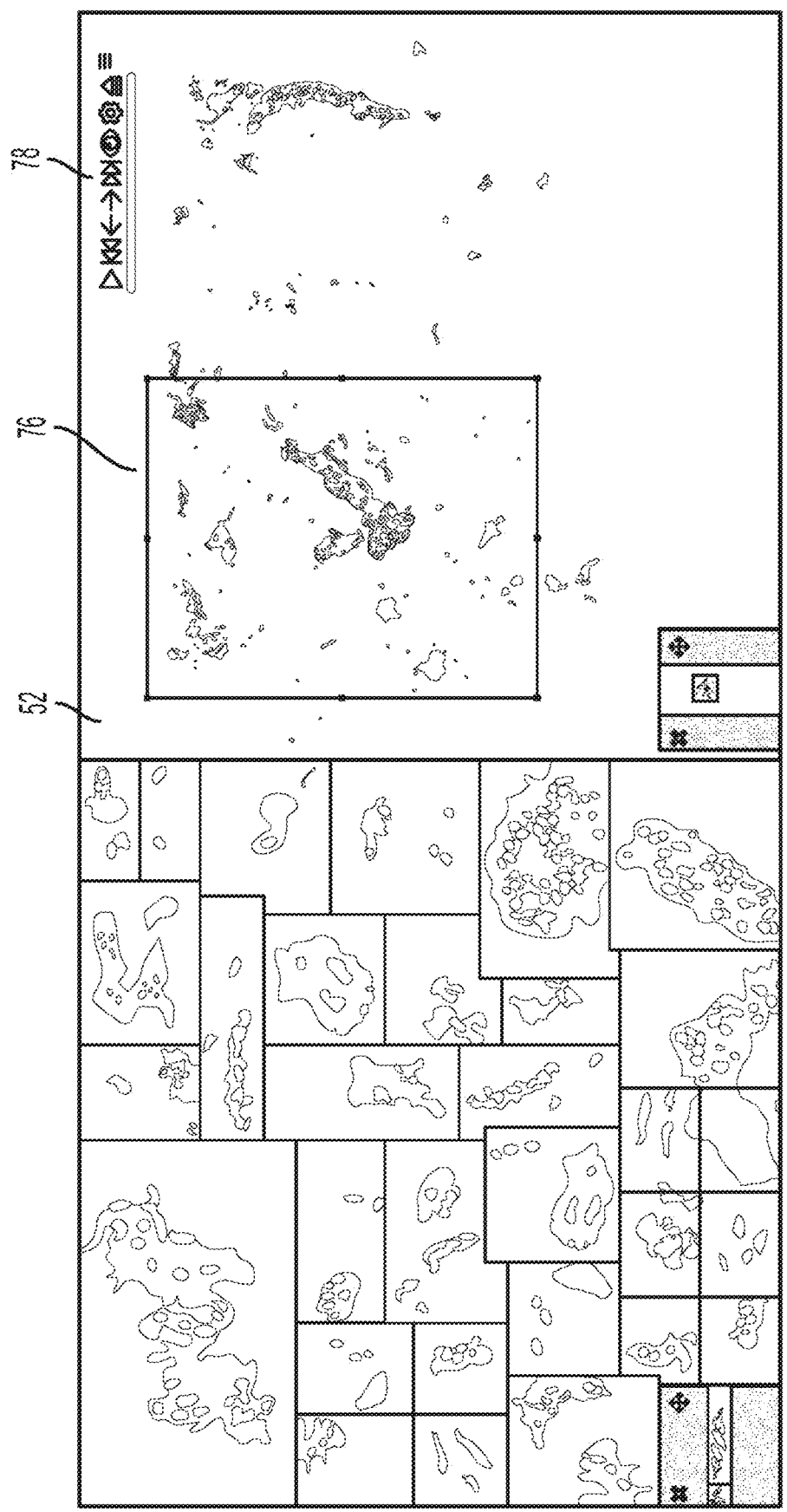
FIG. 15 is a schematic view of a display screen showing a viewing pane which provides a serpentine search feature in accordance with embodiments of the invention.

In embodiments of the invention, the system provides a search window function, which allows a user to dynamically create a subdivision or similar user-defined search areas within the whole slide image. For example, with reference to FIG. 15, the system allows a user to draw a search window 76 using a computer mouse or through a similar command. In embodiments of the invention, the size of the search window 76 is customizable by a user.

In embodiments of the invention, upon initiation of the search feature, the system displays an accompanying toolbar 78 in or near viewing pane 52. In the embodiment shown in FIG. 15, toolbar 78 is shown at the top, right corner of right viewing pane 52. Toolbar 78 contains control icons such as navigation tools which when selected by a user allows a user to navigate within the search window 76.

Figure 16:
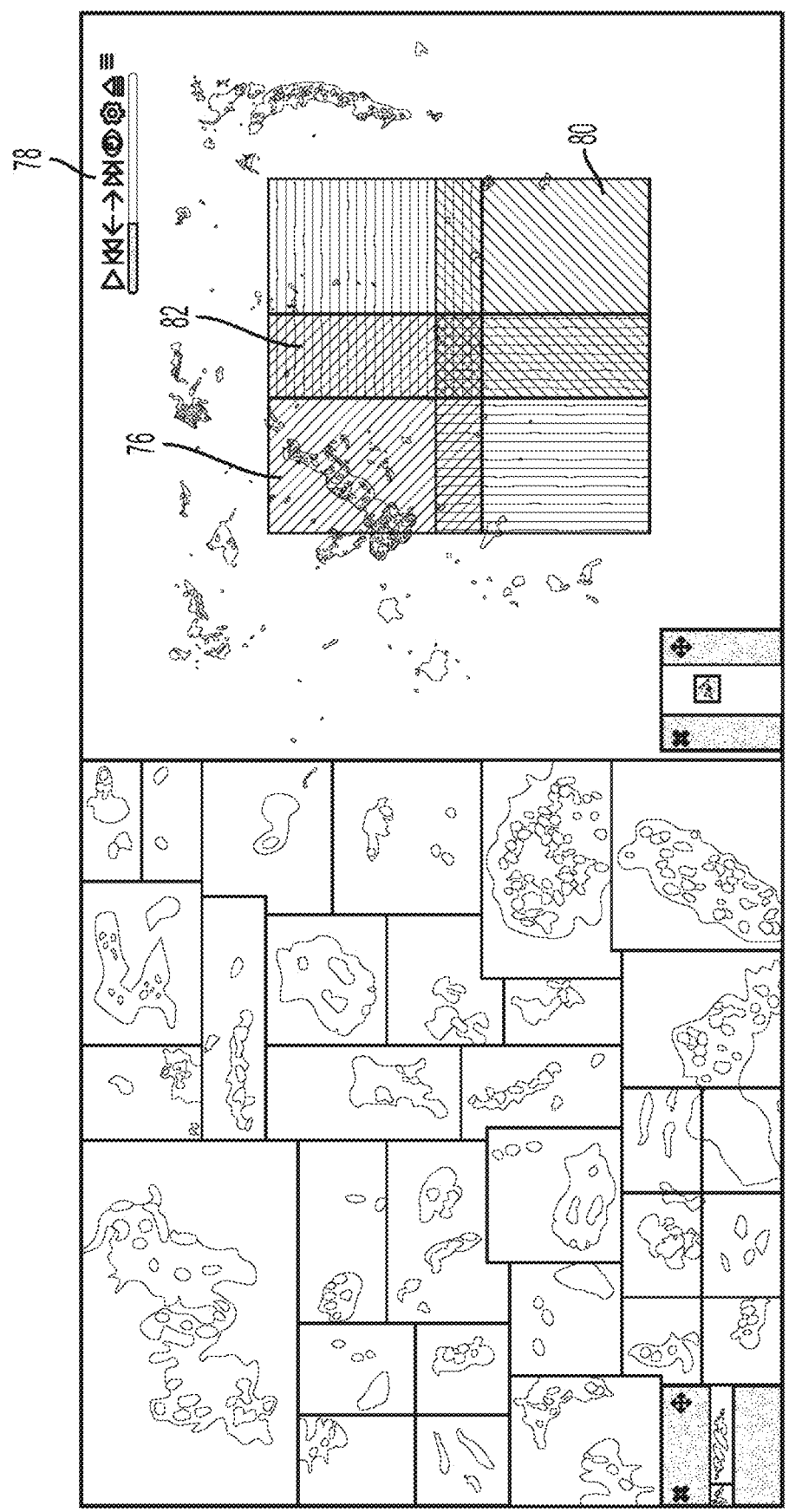
FIG. 16 is a schematic view of a display screen showing a viewing pane which provides a visual tracking system for tracking slide areas that have been viewed by a user in accordance with embodiments of the invention.

In embodiments of the invention, the system tracks and stores each instance that a user navigates to a given area within the search window 76. For example, with reference to FIG. 16, the system provides a map 80 of the user-defined search window 76, in which areas that have been navigated to by a user are shaded and areas that have been navigated to more than once are shaded in a darker color (e.g., 82) than areas navigated to only once. Thus, in embodiments of the invention, the map 80 provides a user with a visual guide of which areas within the search window 76 were reviewed. In embodiments of the invention, the system darkens areas of the map 80 each time a user traverses a given area within search window 76. In this regard, the user is presented with a visual illustration of which areas were reviewed more times than others. In exemplary embodiments, areas may also be selected and marked by the user (e.g. pathologist), for example, as being of potential concern, so not being of potential concern, as requiring further review, or the like. In embodiments, the user may share with others, for example by automatic creation of an email or through automated insertion into a password-protected file directory, a selected set of tiles or regions.

In embodiments of the invention, the system is configured to analyze a slide containing fixed cell block segments. For example, the system digitizes a slide containing cell block slices affixed to the slide and generates a gallery of tiles as set forth herein. As described, because cell block cuts are made in close seriatim, typically, two neighboring cell block slices will be very similar to one another and could even appear to be identical. Thus, in embodiments of the invention, the system provides a pathologist with the ability to compare reactions of a same tissue structure to two different stain or immunohistochemistry markers.

Figure 17:
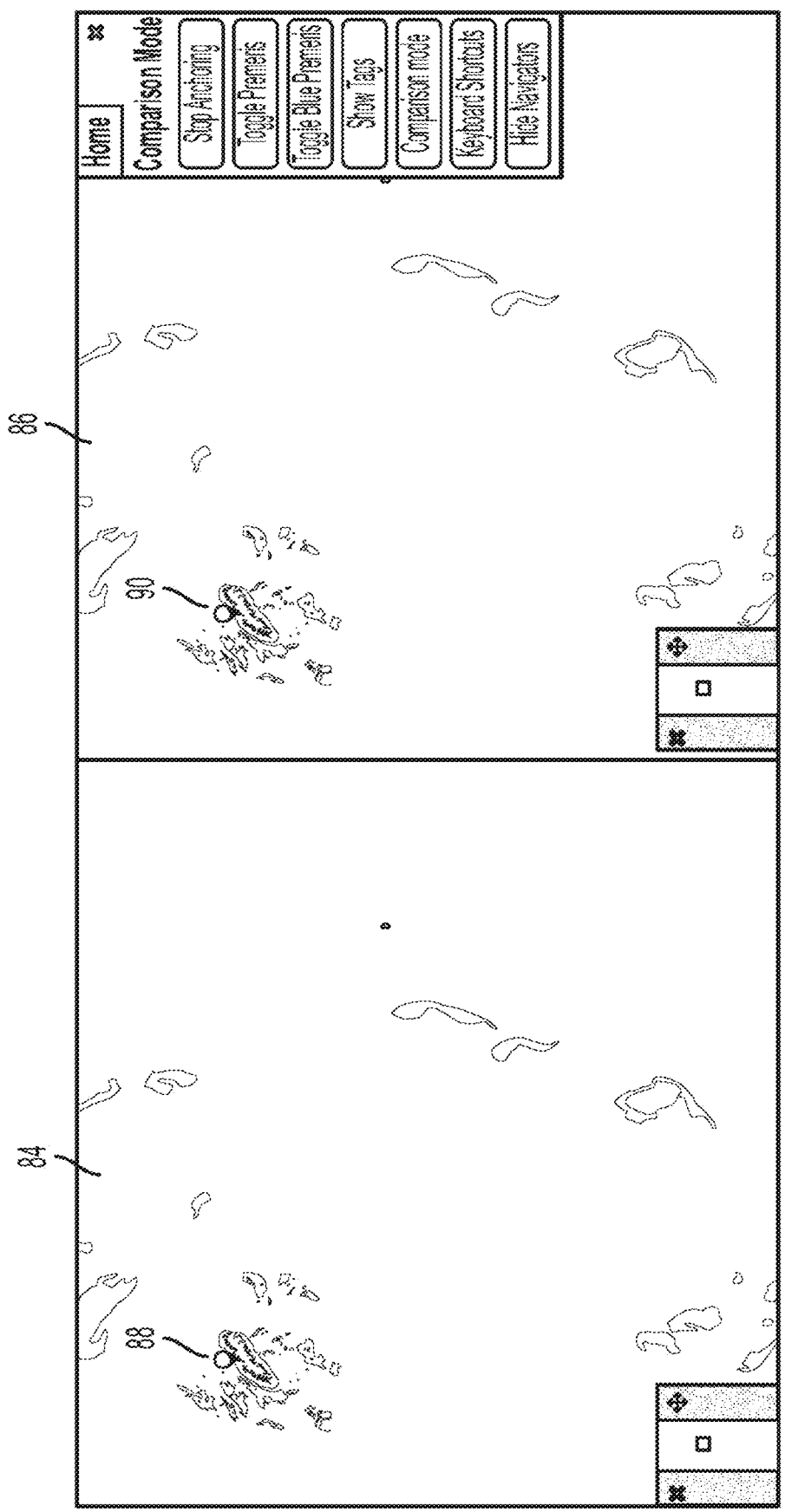
FIG. 17 is a schematic view of two respective sides of a split screen that are configured to move in tandem in accordance with embodiments of the invention, for example allowing simultaneously viewing of corresponding side-by-side views of different stains or other treatments of similarly-composed samples.
Figure 18:
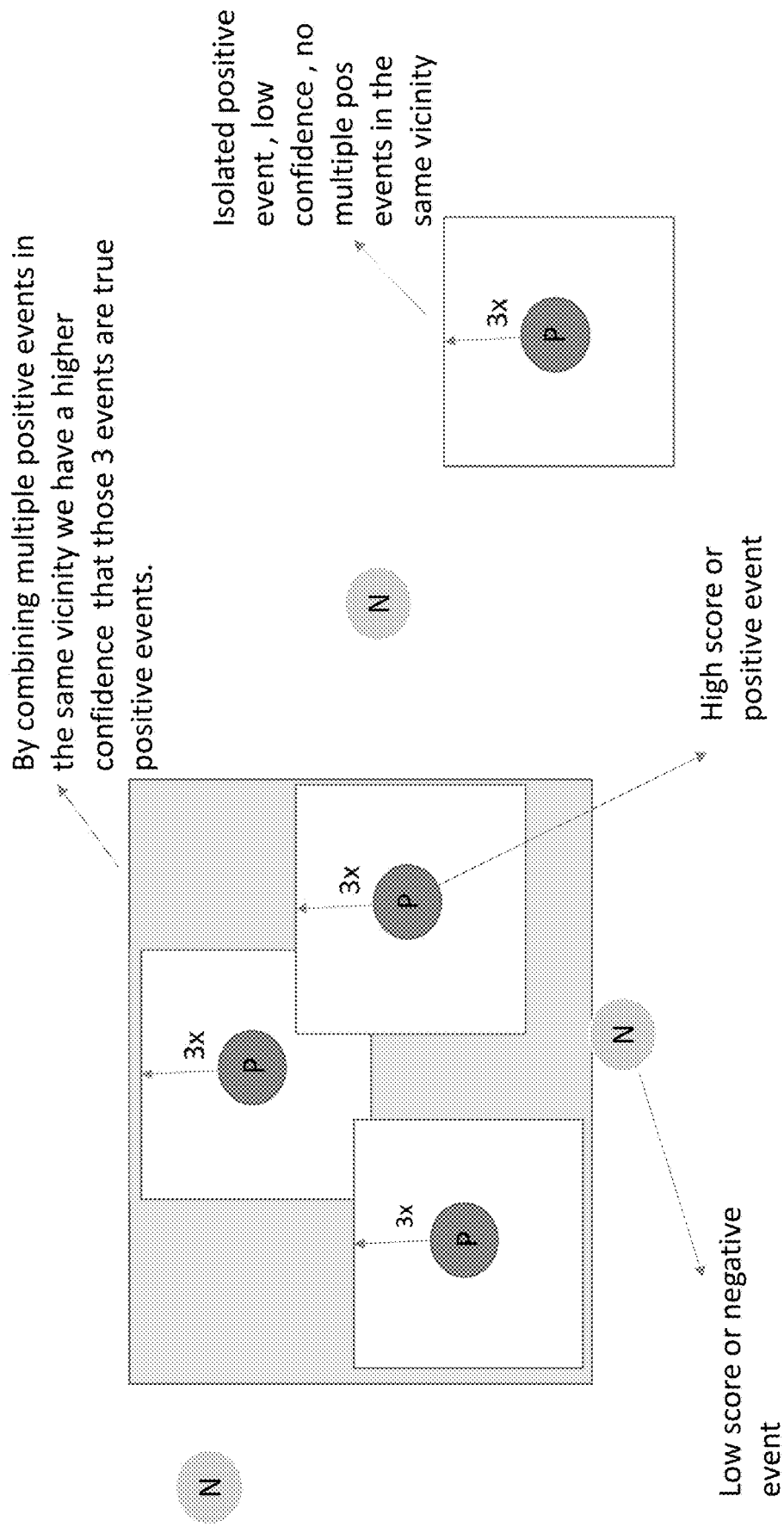
FIG. 18 is a non-limiting example of a vicinity determination and a subsequent selection of a tile to be displayed. The shaded rectangle area is the tile that is displayed as high confidence.

For example, with reference to FIG. 17, a display is shown having a first viewing pane 84 and a second, neighboring viewing pane 86. In embodiments of the invention, a first cell block slice (or a segment thereof) is displayed in first viewing pane 84 and a second cell block slice is displayed in second viewing pane 86. The second cell block slice may be cut either successively with the first cell block slice, or closely within the vicinity of the first cell block slice. As such, the first and second cell block slices contain, substantially, the same tissue and cell structures. Thus, the system may display the first cell block stained with a first stain and the second cell block with a second stain so that a pathologist may view the same tissue area under two different staining conditions in a side-by-side manner.

In embodiments of the invention, the system further provides a user with the ability to move the image displayed in the first and second viewing panes 84, 86 in lockstep. For example, as shown in FIG. 17, the system provides an option for a user to select an anchor point on each respective image in viewing panes 84, 86. As shown, a user may place a first image anchor 88 on a point of the first image, and a second image anchor 90 on a point in the second image, for example, simultaneously, according to selecting the corresponding point in either pane 84, 86. As such, both images will be moved and zoomed simultaneously by a user in order to allow various comparisons and navigation options.

While this invention has been described in conjunction with the embodiments outlined above, it is evident that many alternatives, modifications and variations will be apparent to those skilled in the art. Accordingly, the exemplary embodiments of the invention, as set forth above, are intended to be illustrative, not limiting. Various changes may be made without departing from the spirit and scope of the invention.

What is claimed is:

1. A system for dynamically generating image tiles, comprising:
   an electronic display;
   a storage medium storing a digitized cell specimen containing cells;
   a processor operatively connected to the storage medium and to the electronic display, the processor configured to:
i) access the digitized cell specimen stored in the storage medium;
ii) identify a first abnormal feature associated with a first at least one cell in the digitized cell specimen, and a second abnormal feature associated with a second at least one cell in the digitized cell specimen, through use of a classifier;
iii) calculate, based on the first abnormal feature associated with the first at least one cell, a first score;
iv) calculate, based on the second abnormal feature associated with the second at least one cell, a second score;
v) generate a first area of interest of the digitized cell specimen surrounding the first at least one cell, whereby the size of the first area of interest is calculated by the processor based on the first score;
vi) generate a second area of interest of the digitized cell specimen surrounding the second at least one cell, whereby the size of the second area of interest is calculated by the process based on the second score;
vii) determine whether the first area of interest contacts the second area of interest, based on at least one of (i) a determination that the first area of interest and the second area of interest each comprise a common perimeter portion, and (ii) a determination that the first area of interest and the second area of interest each comprise a common interior portion, and wherein the areas of interest are substantially square and each side dimension of the area of interest is larger than the smallest distance between the peripheral boundary of adjacent cells of the sample but smaller than the distance between clusters of cells within the sample;
viii) selectively, when the determination is that the first area of interest contacts the second area of interest:
  a. combine the first area of interest and the second area of interest into a third area of interest of the digitized cell specimen comprising the first area of interest and the second area of interest; and
  b. display a combined image tile on the electronic display showing the first at least one cell, the second at least one cell, and the third area of interest;
ix) iteratively repeating steps i) to viii) so as to display an additional third area of interest on the electronic display, wherein the third area of interest and the additional third area of interest are ranked for diagnostic significance and the area of interest with greater diagnostic significance is displayed larger than the area of interest with lesser diagnostic significance.

2. The system of claim 1, whereby the processor is further configured to selectively, when the determination is that the first area of interest does not contact the second area of interest, display a first image tile on the electronic display showing the first at least one cell and the first area of interest and display a second image tile on the electronic display showing the second at least one cell and the second area of interest.

3. The system of claim 1, whereby the digitized specimen comprises a cytological specimen.

4. The system of claim 1, whereby the digitized specimen comprises at least one slice of a cell block.

5. The system of claim 1, whereby the first score comprises a neural net score, determined by the computer processor, based on providing an image of the at least one first cell as an input to a neural network trained using a training set comprising a plurality of images of cells tagged with indications of abnormality, the neural net score being the output of the neural network.

6. The system of claim 5, whereby the neural net score is selected by the neural network from a continuum of scores comprising degrees of abnormality.

7. A method of treating a cancer in a subject comprising receiving a diagnosis or identification of a cancer in a specimen from a subject wherein the cancer has been diagnosed or identified in the specimen using the system of claim 1 and administering to the subject an amount of a therapy for the diagnosed or identified cancer; or a method of reducing the likelihood of a cancer or of treating a dysplasia in a subject comprising receiving a diagnosis or identification of a dysplasia in a specimen from a subject wherein the dysplasia has been diagnosed or identified in the specimen using the system of any claim 1 and administering to the subject an amount of a therapy reducing the likelihood of a cancer or of treating a dysplasia.

8. The method of claim 7, wherein the therapy is an anti-cancer small molecule therapy, anti-cancer radiotherapy, anti-cancer chemotherapy, anti-cancer surgery or an anti-cancer immunotherapy or an immunotherapy for dysplasia.

9. The method of claim 7, wherein the cancer is an esophageal cancer or is an oral cancer.

* * * * *